United States Patent
Mazumdar et al.

(10) Patent No.: US 10,444,007 B2
(45) Date of Patent: Oct. 15, 2019

(54) SYSTEMS, APPARATUS, AND METHODS FOR SPECTRAL IMAGING

(71) Applicant: Massachusetts Institute of Technology, Cambridge, MA (US)

(72) Inventors: Yi Chen Mazumdar, St. Charles, MO (US); Ian W. Hunter, Lincoln, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 15/870,920

(22) Filed: Jan. 13, 2018

(65) Prior Publication Data
US 2018/0135970 A1    May 17, 2018

Related U.S. Application Data

(63) Continuation of application No. PCT/US2016/042512, filed on Jul. 15, 2016.
(Continued)

(51) Int. Cl.
*G01J 3/453* (2006.01)
*G01B 11/14* (2006.01)
(Continued)

(52) U.S. Cl.
CPC ............... *G01B 11/14* (2013.01); *G01J 3/26* (2013.01); *G01J 3/2823* (2013.01);
(Continued)

(58) Field of Classification Search
CPC .. G01B 9/02029; G01B 9/0203; G01B 11/14; G01J 3/2823; G01J 3/45; G01J 3/453; G01J 3/4532; G01J 3/4535
See application file for complete search history.

(56) References Cited

U.S. PATENT DOCUMENTS 5,162,872 A    11/1992   Vanasse
5,539,517 A     7/1996   Cabib et al.
(Continued)

FOREIGN PATENT DOCUMENTS

EP    1484575 A1    12/2004
WO    0214782 A1     2/2002
(Continued)

OTHER PUBLICATIONS

Boer, G. et al., "Compact static Fourier transform spectrometer with a large field of view based on liquid-crystal technology", Applied Optics, vol. 41, No. 7, (Mar. 1, 2002), pp. 1401-1407.
(Continued)

*Primary Examiner* — Michael A Lyons
(74) *Attorney, Agent, or Firm* — Smith Baluch LLP

(57) ABSTRACT

A spectral imaging system includes an autocorrelator to generate different autocorrelations when the moving reflector in the autocorrelator is at different positions so as to reconstruct spectral images. The system also includes a position measurement system to measure the actual positions of the moving reflector when autocorrelations are taken. These actual locations, instead of the desired locations in conventional methods, are then used to reconstruct the spectral image. This approach can address the misalignment of the moving reflector from its desired location (due to external disturbances, slow actuator dynamics, and other factors) in conventional spectral imaging techniques and allow the development of high-resolution, high-stability, portable imaging spectrometers for the general public.

24 Claims, 18 Drawing Sheets

Related U.S. Application Data

(60) Provisional application No. 62/192,824, filed on Jul. 15, 2015.

(51) Int. Cl.
  G06K 9/00 (2006.01)
  G01J 3/28 (2006.01)
  G01J 3/26 (2006.01)

(52) U.S. Cl.
  CPC ........ *G01J 3/4535* (2013.01); *G06K 9/00288* (2013.01); *G06K 9/00677* (2013.01); *G06K 9/00718* (2013.01); *G06K 9/00771* (2013.01)

(56) References Cited

U.S. PATENT DOCUMENTS

| | | |
|---|---|---|
| 5,657,122 A | 8/1997 | Curbelo et al. |
| 5,825,493 A | 10/1998 | Mcglynn |
| 6,005,664 A | 12/1999 | Korenberg et al. |
| 6,501,551 B1 | 12/2002 | Tearney et al. |
| 6,580,509 B1 | 6/2003 | Hutchin et al. |
| 7,079,252 B1* | 7/2006 | Debreczeny ....... A61B 5/14532 356/451 |
| 7,092,101 B2 | 8/2006 | Brady et al. |
| 7,359,058 B2 | 4/2008 | Kranz et al. |
| 7,518,728 B2 | 4/2009 | Koo |
| 7,710,574 B2 | 5/2010 | Sin et al. |
| 7,916,303 B2 | 3/2011 | Ronnekleiv et al. |
| 8,203,715 B2 | 6/2012 | Robinson |
| 9,681,798 B2 | 6/2017 | Hunter et al. |
| 2003/0016901 A1 | 1/2003 | Cormack |
| 2003/0202186 A1 | 10/2003 | Chan et al. |
| 2004/0201853 A1 | 10/2004 | Hill |
| 2005/0275847 A1 | 12/2005 | Moshe |
| 2005/0275848 A1 | 12/2005 | Hill et al. |
| 2006/0238773 A1 | 10/2006 | Wellstead et al. |
| 2007/0013916 A1 | 1/2007 | Kim et al. |
| 2009/0213361 A1* | 8/2009 | Vander Rhodes ........ G01J 3/02 356/51 |
| 2011/0199616 A1* | 8/2011 | Cansot .................... G01J 3/453 356/456 |
| 2012/0105844 A1 | 5/2012 | Brady et al. |
| 2013/0120755 A1* | 5/2013 | Harig ................. G01B 11/2441 356/455 |
| 2013/0222790 A1* | 8/2013 | Hirao ................. G01B 9/02061 356/51 |
| 2015/0211926 A1* | 7/2015 | Robinson .............. G01J 3/2823 356/456 |
| 2015/0369667 A1* | 12/2015 | Robinson .............. G01J 3/4535 356/452 |
| 2017/0343415 A1* | 11/2017 | Suess ...................... G01J 3/021 |
| 2018/0073927 A1* | 3/2018 | Kamikake .............. G01N 21/27 |

FOREIGN PATENT DOCUMENTS

| | | | |
|---|---|---|---|
| WO | 2011086357 A1 | 7/2011 | |
| WO | WO-2014190027 A1 * | 11/2014 | ............ G01J 3/0291 |

OTHER PUBLICATIONS

Brady, D. J. et al., "Compressive sampling strategies for integrated Microspectrometers", Intelligent Integrated Microsystems, Proc. of SPIE, vol. 6232, (2006), 9 pages.

Chao, T.H. et al., "Electro-Optic Imaging Fourier Transform Spectrometer", Defense and Security, International Society for Optics and Photonics, (2005), 6 pages.

De Groot, P et al. "Three-dimensional imaging by sub-Nyquist sampling of white-light interferograms", Optics Letters, vol. 18, No. 17 (1993), pp. 1462-1464.

Do, T. T. et al., "Sparsity Adaptive Matching Pursuit Algorithm for Practical Compressed Sensing", Signals, Systems and Computers, 2008 42nd Asilomar Conference on IEEE, (2008), 7 pages.

Feng, P. et al., "Spectrum-Blind Minimum-Rate Sampling and Reconstruction of Multiband Signals", "Spectrum-blind minimum-rate sampling and reconstruction of multiband signals." Acoustics, Speech, and Signal Processing, 1996. ICASSP-96. Conference Proceedings, 1996 IEEE International Conference on. vol. 3. IEEE, (1996), pp. 1688-1691.

Foster, B. et al., "Exact Reconstruction from Periodic Nonuniform Samples", Acoustics, Speech, and Signal Processing, 1995. ICASSP-95., 1995 International Conference on. vol. 2. IEEE, (1995), pp. 1452-1455.

Gehm, M. E. et al., "Adaptive spectroscopy: Towards adaptive spectral imaging", SPIE Defense and Security Symposium. International Society for Optics and Photonics, (2008), 11 pages.

Gregorcic, P. et al., "Quadrature phase-shift error analysis using a homodyne laser interferometer," Optics Express, vol. 18, No. 17, (2009): 16322-16331.

Heintzmann, K. A. Lidke et al., "Double-pass Fourier transform imaging spectroscopy", Optics Express, vol. 12, No. 5, Mar. 8, 2004, pp. 753-763.

Hong, S., "Direct Spectrum Sensing from compressed measurements", Military Communications Conference, Stanford University, 2010-MILCOM, IEEE, (2010), 6 pages.

International Search Report and the Written Opinion of the International Searching Authority, or the Declaration in related PCT Application No. PCT/US2014/38930, filed May 21, 2014, dated Sep. 24, 2014, 11 pages.

International Search Report on Patentability and Written Opinion of the International Searching Authority in related PCT Application No. PCT/US2014/38930, filed May 21, 2014, dated Dec. 3, 2015, 9 pages.

Katz, O. et al., "Compressive Fourier transform spectroscopy" Frontiers in Optics, Optical Society of America, (2010), 5 pages.

Kinast, J. et al., "Adaptive dynamic range matching for spectroscopic measurements", Applied Optics, vol. 48, No. 10, Apr. 1, 2009, pp. 1891-1897.

Korenberg, M. J. et al., "Raman Spectral Estimation via Fast Orthogonal Search", Analyst, vol. 122, (1997), pp. 879-882.

Korenberg, M. J., "A Robust Orthogonal Algorithm for System Identification and Time-Series Analysis", Biological Cybernetics, vol. 60, (1989), pp. 267-276.

Kudenov, M. W. et al., "Compact snapshot birefringent imaging Fourier transform spectrometer", SPIE Optical Engineering+ Applications. International Society for Optics and Photonics, (2010), 11 pages.

Li et al. "Tests of a practical visible-NIR imaging Fourier transform spectrometer for biological and chemical fluorescence emission measurements" Nov. 9, 2009 / vol. 17, No. 23 / Optics Express 21083. 8 pages.

Manzardo, O. et al., "Miniaturized time-scanning Fourier transform spectrometer based on silicon technology", Symposium on Micromachining and Microfabrication. International Society for Optics and Photonics, vol. 24, No. 23, (1999), pp. 1705-1707.

Peck, E. R. et al., "Wavelength or Length Measurement by Reversible Fringe Counting", Journal of the Optical Society of America, vol. 43, No. 6., (Jun. 1953), pp. 505-509.

Solf, C. et al., "Miniaturized LIGA Fourier Transformation Spectrometer", Sensors, 2003. Proceedings of IEEE. vol. 2. IEEE, (2003), 4 pages.

Sun, H. et al., "Adaptive compressive spectrum sensing for wideband cognitive radios" Communications Letters, IEEE, vol. 16, No. 11, (2012), pp. 1812-1815.

Venema, S. C., "A Kalman Filter Calibration Method for Analog Quadrature Position Encoders", Diss. University of Washington, (1994), 99 pages.

Volin, C. E., et al., "High-speed spectral imager of imaging transient fluorescence phenomena", Applied Optics, vol. 37, No. 34, Dec. 1, 1998, pp. 8112-8119.

Wadsworth, W. et al., "Rugged high speed rotary imaging Fourier Transform Spectrometer for industrial use", Environmental and Industrial Sensing. International Society for Optics and Photonics, (2002), 6 pages.

(56) References Cited

OTHER PUBLICATIONS

Wu, L. et al., "A Miniature Fourier Transform Spectrometer by a Large-Vertical-Displacement Microelectromechanical Mirror", Fourier Transform Spectroscopy. Optical Society of America, (2009), 3 pages.
Zhang, H. et al., "Imaging Fourier transform endospectroscopy for in vivo and in situ multispectral imaging", Optics Express, vol. 20, No. 21, (2012), pp. 23349-23360.
Zhao, J. et al., "Multichannel Fourier Transform Raman spectroscopy: Cornbining the Advantages of CCDs with Interferometry." Applied Spectroscopy, vol. 50, No. 9, (1996), pp. 1209-1214.

\* cited by examiner

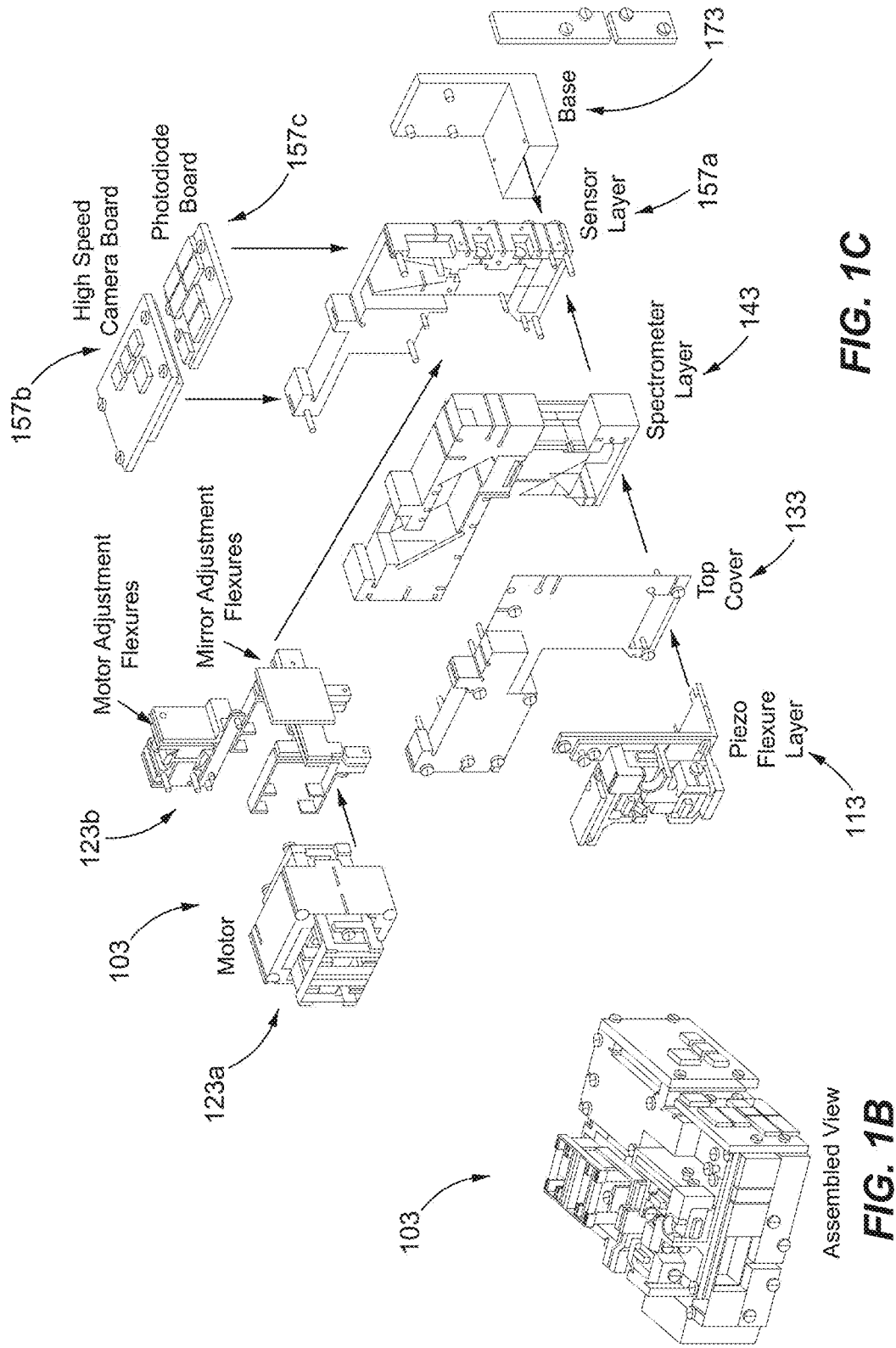

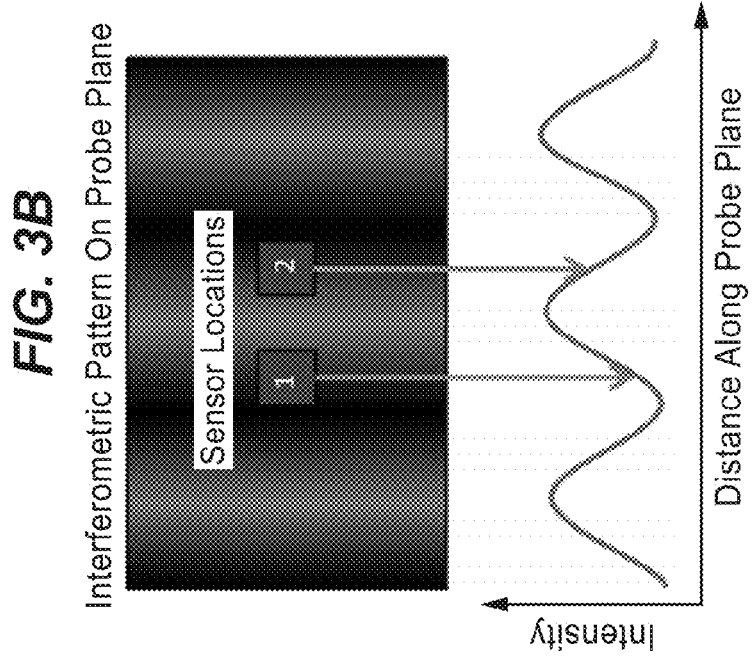
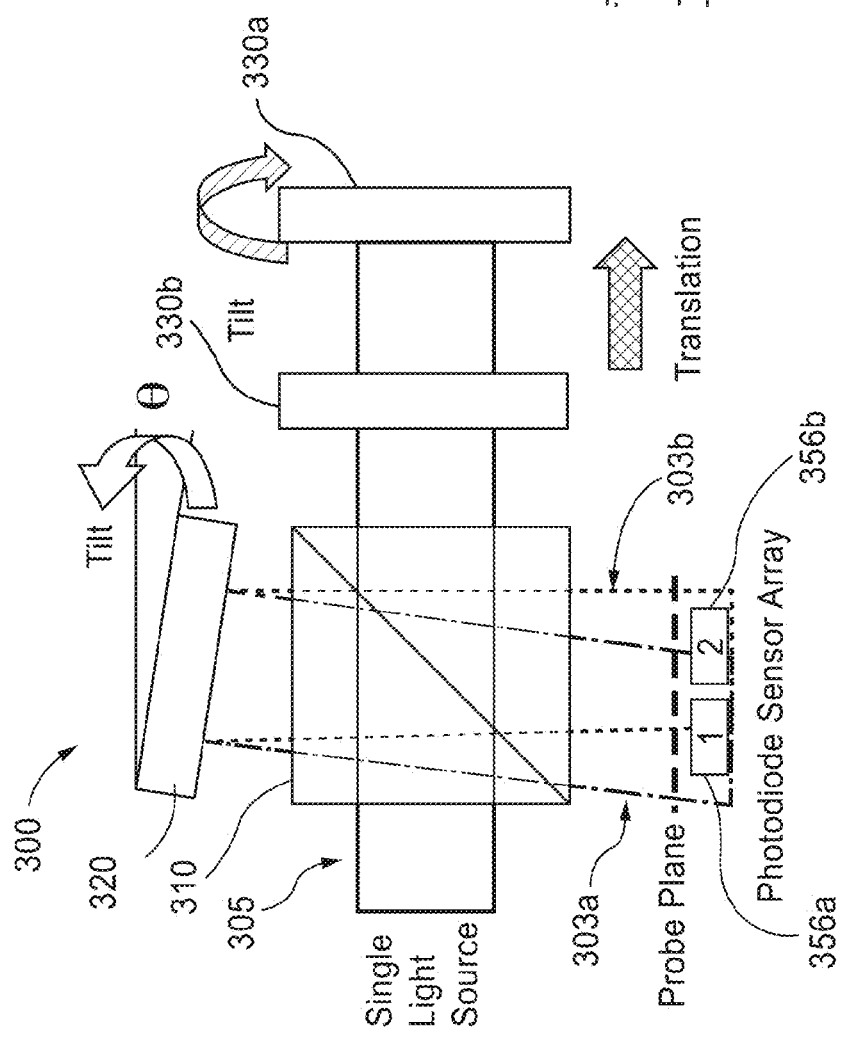

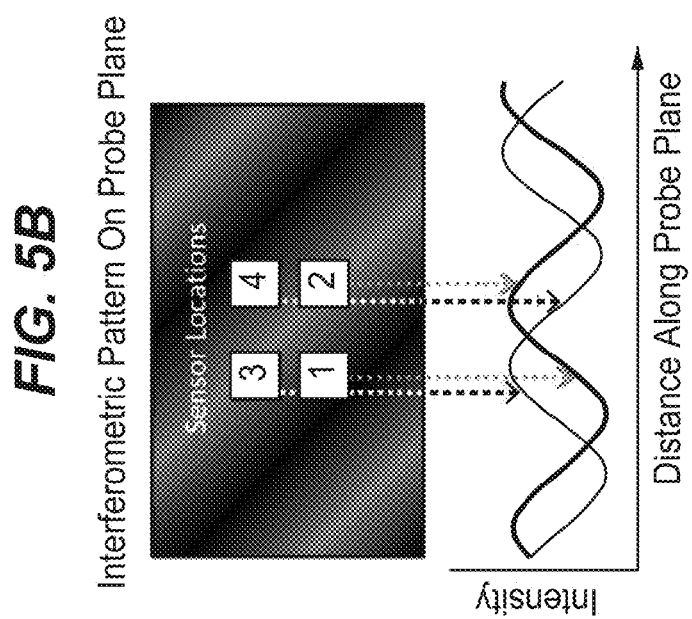
FIG. 5B
FIG. 5C
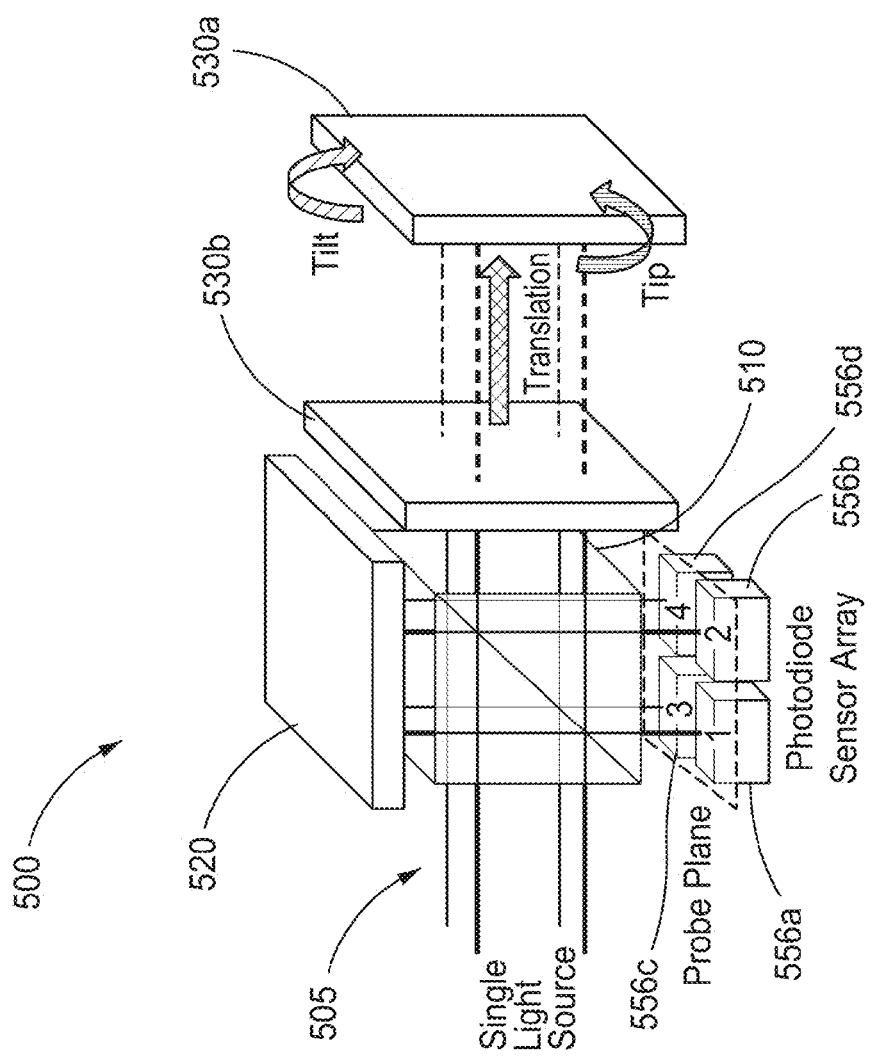
FIG. 5A

SYSTEMS, APPARATUS, AND METHODS FOR SPECTRAL IMAGING

CROSS-REFERENCES TO RELATED APPLICATIONS

This application is a bypass continuation of International Application No. PCT/US2016/042512, filed Jul. 15, 2016, and entitled "SYSTEMS, APPARATUS, AND METHODS FOR SPECTRAL IMAGING," which in turn claims the priority benefit, under 35 U.S.C. § 119(e), of U.S. Application No. 62/192,824, filed Jul. 15, 2015, entitled "MINIATURE, HIGH-SPEED IMAGING TRANSFORM SPECTROMETERS AND ADVANCED SAMPLING ALGORITHMS." Each of these applications is hereby incorporated herein by reference in its entirety.

BACKGROUND

An imaging spectrometer is a device that can take a series of images that include information from a variety of wavelengths of light at fine spectral resolution. When an imaging spectrometer device senses different types of input light, such as ambient light for absorption measurements or laser light for fluorescence or Raman measurements, it can differentiate between materials that are usually indistinguishable to the naked eye in a nondestructive, non-contact manner.

Compared to single-point instruments, an imaging spectrometer can monitor many points at the same time and be much more easily positioned relative to the object of interest, vastly improving usability. The ability to switch between regular and hyperspectral imaging makes it possible to align the spectrometer with respect to the sample without an additional alignment camera. Faster imaging spectrometer systems can be incorporated with image stabilization and object tracking algorithms to account for human or object motion, which can be difficult for a non-imaging system. Being able to select the wavelength resolution on the fly and to obtain high spectral resolution images (e.g., with resolutions of 1.6 cm$^{-1}$ for Raman spectroscopy to 70 cm$^{-1}$ for low resolution spectroscopy) is also desirable for practical applications.

Due to the above advantages, imaging spectrometers can be useful in many applications, such as space probes, biological imaging, air pollution investigation, and health care monitoring, among others. However, existing imaging spectrometers are usually bulky and not readily accessible to the general population, since they are typically mounted to optical tables and include complex components to reject external vibrations.

SUMMARY

Systems, apparatus, and methods described herein are directed to spectral imaging. In one example, a spectral imaging system includes a beam splitter to receive an input light beam reflected or scattered from a sample and to split the input light beam into a first portion and a second portion. A first reflector is in optical communication with the beam splitter to reflect the first portion of the input light beam and a second reflector is in optical communication with the beam splitter to reflect the second portion of the input light beam. The system also includes an actuator, operably coupled to the second reflector, to move the second reflector along a propagation direction of the second portion of the input light beam. A position measurement system is operably coupled to the second reflector to measure a position of the second reflector. A detector is disposed at an intersection between the first portion of the input light beam and the second portion of the input light beam to detect an interference pattern created by the first portion of the input light beam and the second portion of the input light beam. The system further includes a processor, operably coupled to the position measurement system and the detector, to generate a spectral image of the sample based at least in part on the position acquired by the position measurement system and the interference pattern acquired by the detector.

In another example, a method of spectral imaging includes splitting an input light beam reflected or scattered from a sample with a beam splitter into a first portion and a second portion. The method also includes reflecting the first portion of the input light beam with a first reflector and reflecting the second portion of the input light beam with a second reflector. The second reflector is at a first position in a plurality of positions along a propagation direction of the second portion of the input light beam. The method further includes performing measurement of the first position of the second reflector and detecting a first interference pattern created by the first portion of the input light beam and the second portion of the input light beam when the second reflector is at the first position. The method also includes moving the second reflector to a second position in the plurality of positions along the propagation direction of the second portion of the input light beam and performing measurement of the second position of the second reflector. A second interference pattern is created by the first portion of the input light beam and the second portion of the input light beam when the second reflector is at the second position. The method further includes generating a spectral image of the sample based at least in part on the measurement of the first position, the measurement of the second position, the first interference pattern, and the second interference pattern. More spectral images can then be generated by combining the previously acquired interference patterns with additional interference patterns acquired at subsequent actual positions.

In yet another example, a spectral imaging system includes an autocorrelator to create an autocorrelation pattern of an input light beam reflected or scattered from a sample. The autocorrelator includes a beam splitter to split the input light beam into a first portion and a second portion, a first reflector to reflect the first portion of the input light beam, a second reflector to reflect the second portion of the input light beam, and a detector, disposed at an intersection between the first portion of the input light beam and the second portion of the input light beam, to detect an autocorrelation pattern created by the first portion of the input light beam and the second portion of the input light beam. The spectral imaging system also includes a positioning and measurement system operably coupled to the second reflector. The positioning and measurement system includes an actuator to place the second reflector at a plurality of positions non-uniformly spaced along a propagation direction of the second portion of the input light beam. The positioning and measurement system also includes a laser source to emit a probe laser beam toward the beam splitter. The beam splitter directs a first part of the probe laser beam toward the first reflector and directing a second part of the probe laser beam toward the second reflector. An array of photodiodes is in optical communication with the first reflector and the second reflector via the beam splitter to detect a probe interference pattern formed by the first part of the probe laser beam after reflection from the first reflector and the second part of the probe laser beam after reflection from the second reflector. The spectral imaging system further includes a processor, operably coupled to the autocorrelator and the positioning and measurement system, to estimate the plurality of positions of the second reflector based at least in part on the probe interference pattern. The processor also generates a spectral image of the sample based at least in part on the plurality of positions of the second reflector and the autocorrelation pattern of the input light beam.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

BRIEF DESCRIPTION OF THE DRAWINGS

The skilled artisan will understand that the drawings primarily are for illustrative purposes and are not intended to limit the scope of the inventive subject matter described herein. The drawings are not necessarily to scale; in some instances, various aspects of the inventive subject matter disclosed herein may be shown exaggerated or enlarged in the drawings to facilitate an understanding of different features. In the drawings, like reference characters generally refer to like features (e.g., functionally similar and/or structurally similar elements).

FIGS. 1B and 1C show an example implementation of the imaging system shown in FIG. 1A.

FIG. 3A shows a schematic of a reflector position measurement system using two-signal encoders.

FIGS. 3B and 3C illustrate measurement of reflector positions and tilt using the system shown in FIG. 3A.

FIG. 5A shows a schematic of a reflector position measurement system using four-signal encoders.

FIGS. 5B and 5C illustrate measurements of reflector positions, tip, and tilt using the system shown in FIG. 5A.

DETAILED DESCRIPTION

Overview

Figure 1A:
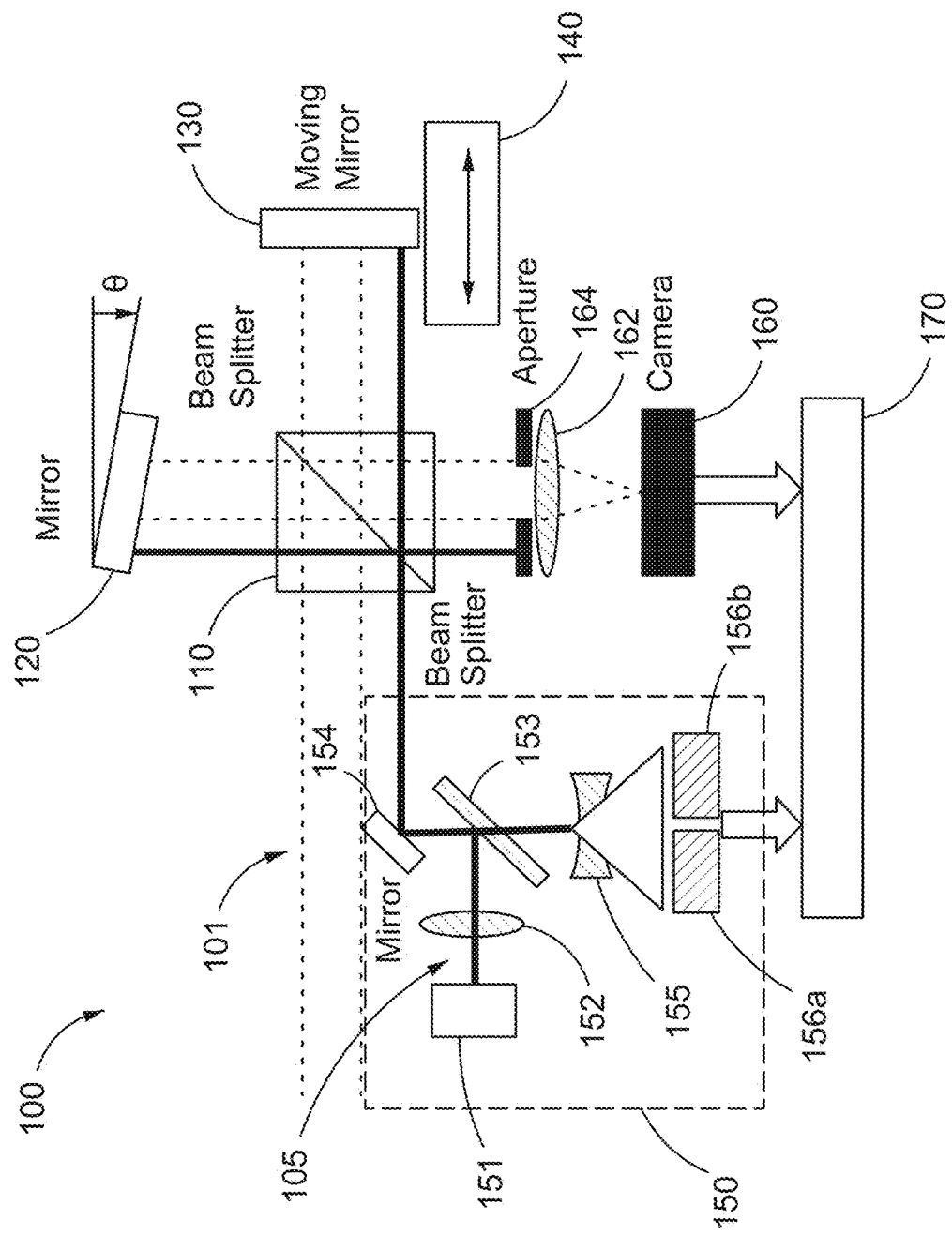
FIG. 1A shows a schematic of spectral imaging systems including a position measurement system.

As introduced above, an imaging spectrometer, such as a Fourier transform spectrometer, usually takes several data points at different autocorrelations of the input light. Autocorrelations of the input light can be achieved using an autocorrelator including a beam splitter to split the input light into two portions and two reflectors, each of which reflects a corresponding portion of the input light toward a detector. The two portions, after reflection by the two reflectors, then combine at the detector to form an interference pattern (also referred to as an autocorrelation pattern). By moving one of the reflectors (also referred to as the moving reflector) to different locations, different autocorrelations can be acquired. A spectral image can then be reconstructed using the different autocorrelation patterns acquired when the moving reflector is at different locations.

In conventional spectral imaging, the moving reflector is usually moved by a motor to a series of desired locations and the subsequent reconstruction of the spectral image also uses these desired locations of the moving reflector. In addition, these desired locations of the moving reflector are also uniformly spaced to simplify actuation and subsequent calculation during reconstruction. However, the actual location of the moving reflector usually deviates from the desired location, due to, for example, mechanical vibration, slow motor dynamics, thermal misalignment, or a combination thereof. The deviation of the actual location in turn can decrease the accuracy of the reconstructed spectral image.

One way to address the misalignment of the moving reflector is to increase the precision and increase the bandwidth of the motor that drives the moving reflector. For example, a piezoelectric actuator can be used to fine tune the position of the moving reflector. The actuator speed is usually faster than the image acquisition rate such that each image can be taken when the moving reflector is at a distinct location. For example, if the desired frame rate (spectral sampling rate) is 2000 fps, then the actuator bandwidth can be about 2 kHz to about 20 kHz or more. As the acquisition rate of the imaging spectrometer increases, it can be challenging for piezoelectric actuators to operate at sufficiently high speeds due to the limitations imposed by, for example, the finite response time of piezoelectric materials or other limitations on the mechanical components in the piezoelectric actuator. In addition, high-speed piezoelectric actuators can be costly and bulky as well, thereby further hindering the miniaturization of the imaging spectrometers.

Systems, apparatus, and methods described herein employ another approach to address the misalignment of the moving reflector. Instead of improving the movement accuracy of the moving reflector using expensive and bulky actuators, this approach takes into account the position deviations of the moving reflector when reconstructing of the spectral image. More specifically, the approach uses a position measurement system to measure the actual locations of the moving reflector when autocorrelation images are taken by the imaging spectrometer. These actual locations, instead of the desired locations in conventional methods, are then used to reconstruct the spectral image using the autocorrelation images. In other words, this approach lives with inaccuracies in the positions of the moving reflector and can tolerate a wide range of misalignment of the moving reflector from its desired locations.

Using actual locations of the moving reflector for image reconstruction can allow the development of miniature, portable imaging spectrometers that have the relatively high spectral resolutions for making scientific measurements without some of the burdensome vibration rejection components. The spectrometer can also be mounted inside other packages, such as an endoscope, smart phone, scanner gun, microscope, or telescope. A spectrometer that can be small enough to fit in the palm of the hand or at the end of an endoscope would enable a host of new applications.

FIG. 1A shows a schematic of a spectral imaging system 100 including a position measurement system 150. The system 100 includes a beam splitter 110 to receive input light 101, which can be light reflected, scattered, or emitted from an object or scene to be imaged. The beam splitter 110 divides the input light 101 into two portions. The first portion is directed by the beam splitter 110 to a first reflector 120 and the second portion is directed to a second reflector 120. The two reflectors 120 and 130 reflect the corresponding portion of the input light beam 101 toward an aperture 164 and a lens 162 behind the aperture 164. A detector 160, placed at the focal plane of the lens 162, detects interference patterns (also referred to as autocorrelation patterns in this example) created by the first portion and the second portion of the input light 101.

An actuator 140 is coupled to the second reflector 130 (also referred to as the moving reflector) to move the second reflector 130 to different positions along the propagation direction of the second portion of the input light 101. At each position of the moving reflector 130, the detector 160 can take one or more autocorrelation patterns. A processor 170 is in communication with the detector 160 to receive the autocorrelation patterns acquired by the detector 160 and to generate a spectral image of the object based on these autocorrelation patterns.

The position measurement system 150 shown in FIG. 1A employs an optical technique to determine the position of the reflector 130. The position measurement system 150 includes a laser 151 to provide a probe laser beam 105 (or simply probe beam 105), which propagates to a lens 152 for collimation before arriving at a probe beam splitter 153. Part of the probe beam 105 is reflected by the probe beam splitter 153 toward a mirror 154, which further reflects the probe beam 105 toward the beam splitter 110. The probe laser beam 105 then travels through a similar beam path as travelled by the input light 101. More specifically, the first reflector 120 reflects one part of the probe laser beam 105 and the second reflector 130 reflects another part of the probe laser beam 105. The two parts of the probe laser beam, after reflection by the corresponding reflector 120/130, propagate back to the mirror 154 and through the probe beam splitter 153. A negative lens 155 then expands the probe laser beam 105. Two probe detectors 156a and 156b are placed after the negative lens 155 to detect the interference pattern generated by the two parts of the probe laser beam 105.

In one example, the laser 151 can include a HeNe laser. In another example, the laser 151 can include a Nd:YAG laser with a frequency doubling crystal to deliver laser beams at 532 nm. In yet another example, the laser 151 can include a vertical-cavity surface-emitting laser (VCSEL). For example, a surface mount 0603 package VCSEL at 850 nm with a bandwidth of about 0.057 nm to about 0.1 nm full-width-at-half-maximums (FWHM) can be used as the laser 151. The spectral resolution of the system 150 using this VCSEL laser can be about 1.38 $cm^{-1}$ to 0.788 $cm^{-1}$ without the use of any spectral line correction algorithms. This small laser would also enable the miniaturization of the imaging spectrometer.

It can be desirable for the laser 151 to emit the probe laser beam 105 with a narrow linewidth. In general, a narrower linewidth of the probe laser beam 105 can lead to a finer resolution position measurement of the moving reflector 130. In one example, the linewidth of the probe laser beam 105 can be less than 5 nm (e.g., less than 5 nm, less than 3 nm, less than 2 nm, or less than 1 nm, including any value and sub ranges in between). In another example, the linewidth of the probe laser beam 105 can be less than 0.5 nm (e.g., less than 0.5 nm, less than 0.3 nm, less than 0.2 nm, less than 0.1 nm, less than 0.08 nm, or less than 0.05 nm, including any values and sub ranges in between).

The position and tilt of the reflectors 120 and 130 can be determined as follows. When one reflector (e.g., 120) is tilted with respect to the other reflector (e.g., 130), the paths of the probe laser beam 105 reflected from those two reflectors 120 and 130 change accordingly, thereby projecting an interference pattern on the probe plane. This interferometric pattern can be sinusoidal with a period that is a function of the relative position of the two reflectors 120 and 130 as well as the relative tilt. When the moving reflector 130 is translated, the dark and bright portions of the light can translate left or right. By placing the two photodiodes 156a and 156b at different locations on this interferometric pattern, it is possible to measure two parts of this sinusoidal curve with a fixed phase delay. With two signals, it is possible to calculate the position and direction of propagation by using an analog encoder scheme where the phase delay resulting from a tilt angle is found through calibration (see, e.g., FIGS. 3A-4B).

The two detectors 156a and 156b are also in communication with the processor 170, which can determine the actual positions of the moving reflector 130 from the detector measurements. In addition, using the actual positions of the moving reflector 130, the processor 170 can further reconstruct the spectral image of the object. Since the actual positions of the moving reflector 130 can be accurately monitored by the position measurement system 150 and used in subsequent spectral image reconstruction, potential misalignment of the moving reflector 130 may no longer be a concern to users.

In FIG. 1A, the system 100 uses a single-pass Michelson interferometer to generate autocorrelation patterns of the input light 101. In practice, several other configurations can also be used to generate autocorrelation. In one example, the system 100 can use a double-pass Michelson interferometer to generate autocorrelation of the input light 101. In another example, a common path Sagnac can be used to generate autocorrelation of the input light 101. In yet another example, the system 100 can use an electro-optic modulator style interferometer. More details about different types of autocorrelator can be found in U.S. patent application Ser. No. 14/933,666, entitled "Methods, systems, and apparatus for imaging spectroscopy," which is hereby incorporated herein by reference in its entirety.

Figure 1D:
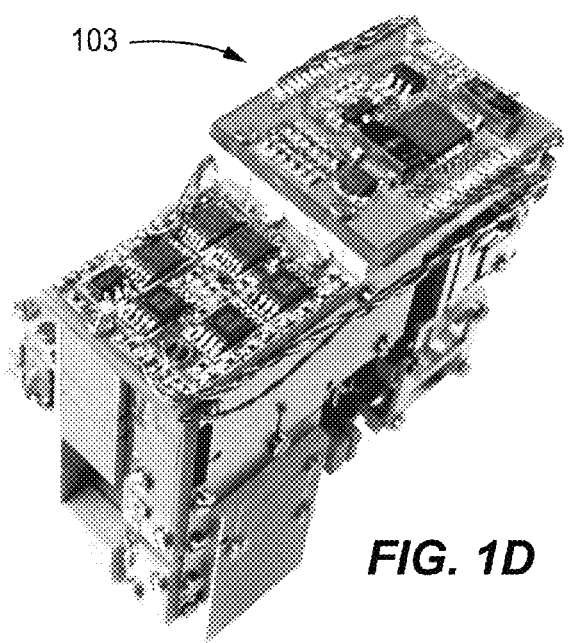
FIGS. 1D and 1E illustrate a full spectrometer system including electronics.
Figure 1E:
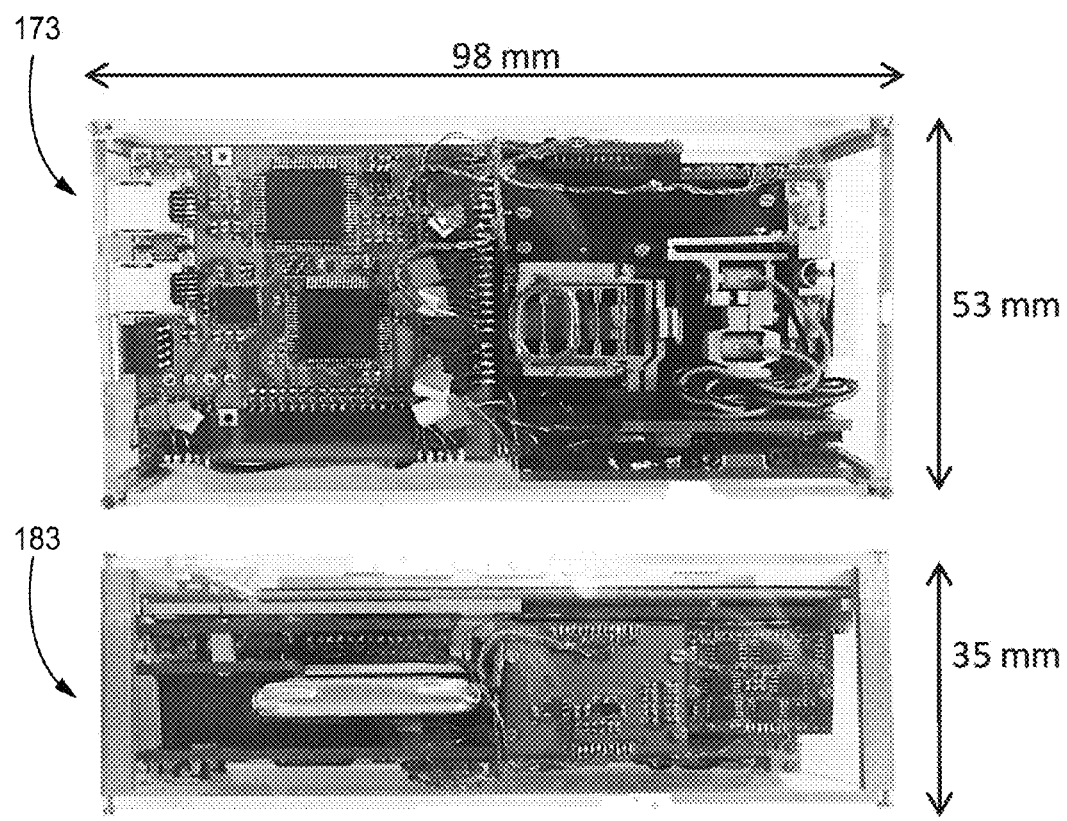

FIGS. 1B and 1C show an assembled view and an exploded view, respectively, of an imaging device 103 that can use the imaging system 100 shown in FIG. 1A. The device 103 includes a spectrometer layer 143 that can include optical setup similar to that shown in FIG. 1A. A sensor layer 157a including high speed camera board 157b and a photodiode board 157c (collectively referred to as sensors 157) are coupled to the spectrometer layer 143a to detect autocorrelation patterns created in the spectrometer layer 143. The sensors 157 can also measure positions of reflectors in the spectrometer layer 143 so as to facilitate subsequent image reconstruction. A motor 123a and motor adjustment flexures 123b (collectively referred to as motors 123) are coupled to the spectrometer layer 143 to move the reflectors in the spectrometer layer 143. The motors 123 and the sensors 157 are coupled to opposite sides of the spectrometer layer 143 so as to effectively use the space in the device 103. The device 103 also includes a piezoelectric flexure layer 113 to adjust the tip, tilt, and translation of the reflectors in the spectrometer layer 143 at higher precisions. The device 103 further includes a top cover 133 and a base 163 to enclose the various components, thereby resulting in a compact and portable device 103 as shown in FIG. 1B. FIG. 1D shows a photo of the imaging device 103 described above. FIG. 1E shows the full embodiment including processing electronics 173 and power electronics 183 in a hand-held format.

Actuators to Move the Reflector

The actuator 140 in the system 100 is for moving the moving reflector 130. In practice, it can be desirable for the actuator 140 to travel at least several millimeters, have a positioning resolution on the order of micrometers, and have a high bandwidth to move quickly. Traditionally, imaging spectrometers sweep through the different positions of the moving reflector and control only the speed at which the actuator moves, without controlling the positions. These spectrometers typically use fast sampling on fast photodiodes in a continuous fashion. In contrast, the system 100 takes snapshots rather than continuous data. Therefore, it can be desirable to hold the moving reflector 130 in position during each snapshot (also referred to as exposure time for each image).

Since the approach described herein uses actual positions of the moving reflector 130 to reconstruct the spectral image, the requirements on the position resolution of the actuator 140 can be relaxed and the actual positions of the moving reflector 130 can be spaced non-uniformly. In one example, the variation of the spacing between adjacent positions of the moving reflector 130 can be more than 10%. In another example, the spacing variation can be greater than 50%. In yet another example, the spacing variation can be greater than 100% (e.g., greater than 100%, greater than 150%, greater than 200%, or greater than 250%). In principle, this approach can allow any spacing of the actual positions of the moving reflector 130. The actual positions can also be under-sampled (i.e., sampled at a lower frequency than the Nyquist frequency, see sections below). One theoretical limitation can be based on information content. For example, the moving reflector 130 can be placed at a plurality of non-uniformly spaced positions with sufficient informational content to allow for a unique solution when reconstructing the spectral image.

The actuator 140 can operate at various frequencies, which can be defined as the number of movements made by the moving reflector 130 per second. For example, the actuator 140 can operate at a speed greater than 20 Hz (e.g., greater than 20 Hz, greater than 30 Hz, greater than 50 Hz, greater than 100 Hz, greater than 150 Hz, greater than 200 Hz, greater than 300 Hz, greater than 500 Hz, greater than 750 Hz, greater than 1000 Hz, or greater than 2000 Hz, including any values and sub ranges in between).

The detector 160 can operate at similar frame rate to acquire image each time the moving reflector 130 is placed at a different position. For example, the detector 160 can acquire images at a frame rate greater than 20 frames per second (fps) (e.g., e.g., greater than 20 fps, greater than 30 fps, greater than 50 fps, greater than 100 fps, greater than 150 fps, greater than 200 fps, greater than 300 fps, greater than 500 fps, greater than 750 fps, greater than 1000 fps, or greater than 2000 fps, including any values and sub ranges in between).

The actuator 140 can also operate at various step sizes. For example, the step size of the actuator 140 can be substantially equal to or greater than 0.1 µm (e.g., 0.1 µm, 0.2 µm, 0.3 µm, 0.5 µm, 0.8 µm, 1 µm, 1.2 µm, 1.5 µm, 2 µm, 3 µm, 5 µm, or longer, including any values and sub ranges in between). In practice, the step size can depend on the characteristics of the actuator 140. For example, if the dynamics are slow (for example, a slow slew rate), then the step sizes can be small. If the dynamics are faster (for example, a fast slew rate), the step sizes can be larger. One region of steps sizes, in which approaches described herein can be advantageous, is where the measured position is sufficiently different from the desired position. Sufficiently different is when the deviation of the desired position is a significant proportion of the wavelength of interest. For example, if the wavelength of interest is 500 nm and the desired wavelength accuracy is better than 20 nm, then the desired positioning accuracy should be better than 10 nm. If the positioning accuracy of the actuator 140 is worse than 10 nm, then conventional methods may not work, but approaches described herein can still use the actuator 140 because potential misalignment is addressed in the subsequent reconstruction stages. In other words, approaches described herein can use actuators that may not otherwise usable in conventional spectral imaging methods.

The dynamic range of the actuator 140 (also referred to as the range of travel) can depend on, for example, the desired spectral resolution of the system 100. In general, a larger range of travel can lead to finer spectral resolution. For example, the rage of travel of the actuator 140 can be about 0.1 mm to about 10 mm (e.g., 0.1 mm, 0.2 mm, 0.3 mm, 0.4 mm, 0.5 mm, 0.7 mm, 1.0 mm, 1.2 mm, 1.5 mm, 2 mm, 3 mm, 5 mm, 8 mm, or 10 mm, including any values and sub ranges in between).

Voice Coil Motors for Moving Mirrors

Figures 2A, 2B:
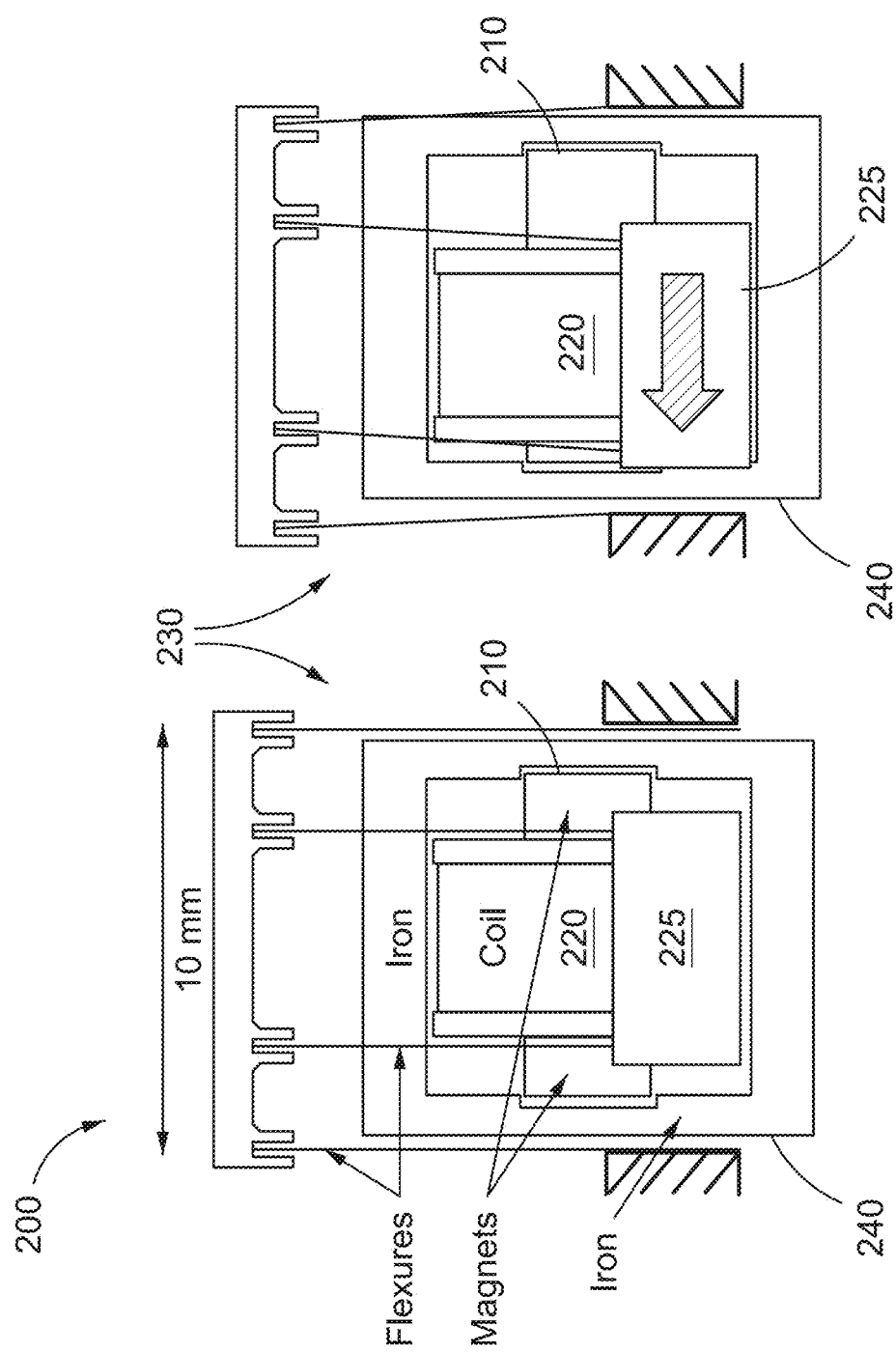
FIGS. 2A-2B shows a schematic of a motor design that can be used to move reflectors in the system shown in FIG. 1A.

FIGS. 2A-2B show schematics of motor 200 that can be used as the actuator 140 in the system 100. The motor 200 includes one or more permanent magnets 210 disposed within a coil 220 that is disposed on a coil holder 225 (also referred to as a bobbin). The magnets 210 and the coil 220 are enclosed in a housing 240 (which is also the back iron or actuator yoke of the motor which steers the magnetic field lines). Four flexures 230 are located on each side of the actuator and suspend the coil 220 via the coil holder 225 such that there is little to no friction between the bobbin of the coil 220 and the housing 240. The flexures 230 also function as a return spring to move the coil 220 back to its original position after when needed. In operation, if no current is applied to the coil 220, as shown in FIG. 2A, the coil 220 stays in the middle of the housing 240. When an electric current is applied to the coil 220, the Lorenz force between the magnets 210 and the coil 220 can displace the coil 220, as illustrated in FIG. 2B. Therefore, the motor 200 is also referred to as a linear Lorenz force voice coil motor.

The motor 200 can be relatively small for a desired stroke (i.e., range of movement of the coil 220). It can also operate with relatively low friction, which may cause unpredictable parasitic rotation on the reflectors. In addition, the motor 200 uses a cube-like geometry, which can be manufactured using wire electrical discharge machining (EDM), can be easy to assemble, and can easily accommodate high rotational-stiffness blade flexures. By attaching reflectors at some point closer to the coil 220, the resulting imaging spectrometers can also be made smaller.

In one example, the housing 240 (sometimes also referred to as an actuator yoke) can be made from low-carbon 1018 steel, which typically has a high magnetic permeability. The flexures 230 can be made from thin 300 series stainless steel shim stock, which can be manufactured with a wire EDM if clamped to thicker pieces of metal on the top and bottom. Although this material may be slightly paramagnetic, the high yield strength to Young's modulus ratio makes it a suitable material for blade flexures.

Figure 2C:
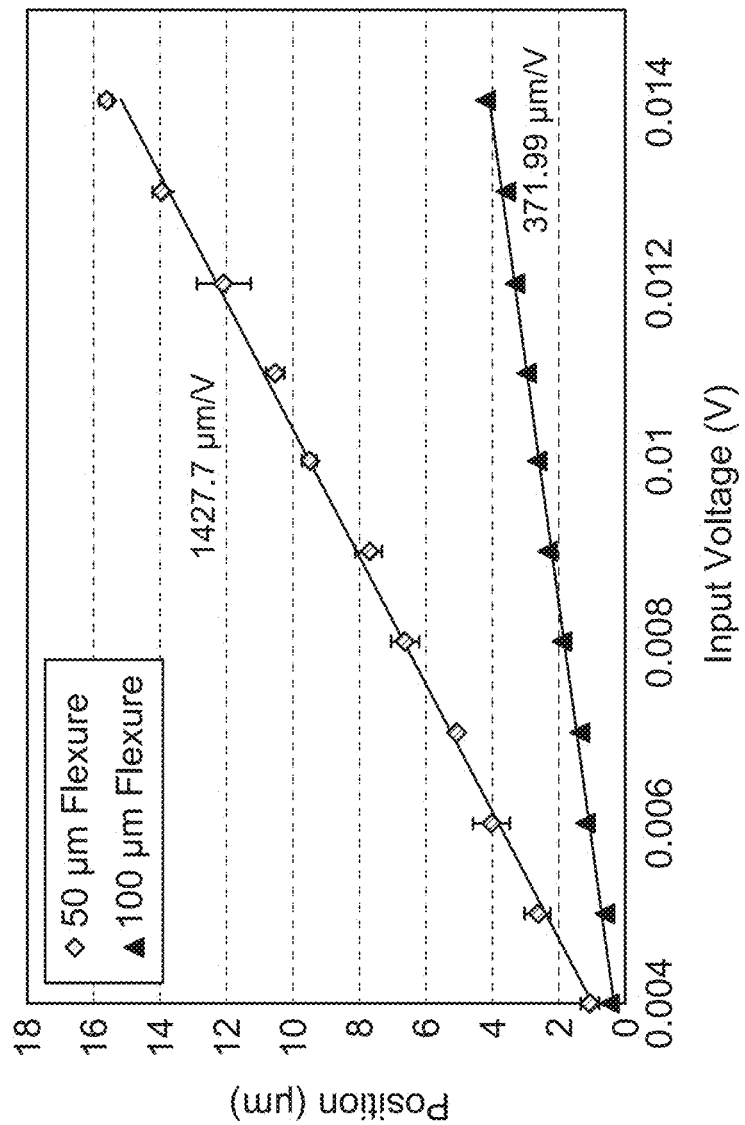
FIG. 2C shows experimental results of linear translations of the motor shown in FIGS. 2A-2B as a function of input voltage.

FIG. 2C shows experimental results of linear translation of the motor 200 as a function of input voltage to the motor for different blade flexure thicknesses. In general, thicker flexures can make it more difficult to move the coil 220, at a given applied voltage. As shown in FIG. 2C, a motor having 50 μm thick flexures can move 1427.7 μm per applied volt and a motor having 100 μm can move 371.99 μm per applied volt. The motor 200 can have a resolution on the order of 1 μm or finer (e.g., 0.5 μm, 0.3 μm, 0.1 μm, 50 nm, 10 nm, 0.1 nm or finer).

In addition to the voice coil motor 200 illustrated in FIGS. 2A-2C, several other types of actuators can also be used to move the moving reflector in the imaging system 100. In one example, the system 100 can use stepper motors. In another example, the system 100 can use Microelectromechanical system (MEMS) pop-up mirrors. More information of MEMS pop-up mirrors can be found in U.S. Pat. No. 6,396,975, entitled "MEMS optical cross-connect switch," which is hereby incorporated herein by reference in its entirety. In yet another example, the system 100 can use rotary to linear conversion motors.

Figures 2D, 2E:
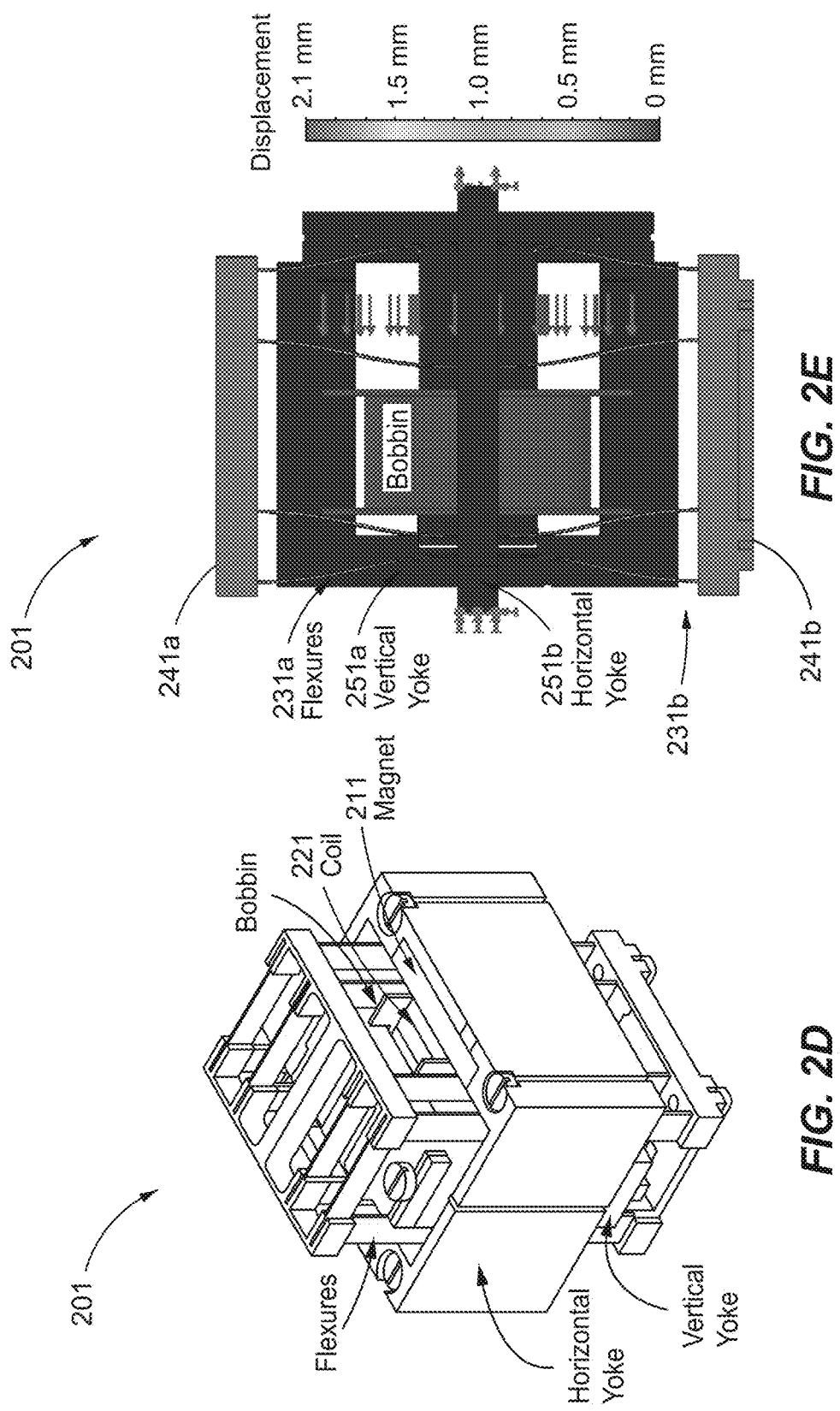
FIGS. 2D and 2E show a schematic of a motor including symmetric flexures with more output force, higher stiffness, and more symmetric motion that can be used to move reflectors in the system shown in FIG. 1A.

FIGS. 2D and 2E show a perspective view and a side view, respectively, of a motor 201 that can be used as the actuator 140 in the system 100. The motor 201 includes one set of flexures 231a coupled to a top housing 241a and a second set of flexures 231b coupled to a bottom housing 241b. The flexures 231a and 231b are coupled to the coil 221 on opposite sides of the coil 221. This configuration using two sets of flexures 231a and 231b can increase stiffness, increase speed, and improve symmetry in the motion. The motor 201 also includes two sets of yokes: a vertical yoke 251a and a horizontal yoke 251b to increase the output force. A magnet set 211 is placed directly into the yoke 251a and 251b to increase the magnetic field magnitude and hence the force produced at the coil 221.

Measurement of Reflector Positions Using Two-Signal Encoders

The position measurement system 150 in the system 100 can use analog encoders to determine location and tilt of the reflectors 120 and/or 130. An analog encoder basically includes an array of detectors (e.g., detectors 156a and 156b), such as photodiodes placed in the interference pattern generated by the probe laser beam 105. In one example, the analog encoders can include two detectors placed in a one-dimensional array. In another example, the analog encoders can include four detectors placed in a 2×2 array. In yet another example, the analog encoders can include any other configurations such as a 2×3 array, a 2×4 array, or a 3×4 array, among others.

FIG. 3A shows a schematic of a position measurement system 300 using two-signal encoders. The system 300 includes a beam splitter 310 to receive a probe beam 305 and divide the probe beam 305 into two parts. One part of the probe beam 305 is reflected by a first reflector 320 and the other part of the probe beam 305 is reflected by a second reflector 330. The first reflector 320 can have a tilt angle θ, and the second reflector 330 can move between two positions 330a and 330b. The two parts of the probe beam 305 after reflections from the corresponding reflector 320 and 330 are combined by the beam splitter 310 and directed to two detectors 356a and 356b, which sense interference patterns generated by the two parts of the probe beam 305.

FIG. 3B shows an example of an interferometric pattern in the probe plane where the two detectors 356a and 356b are placed. The locations of the two detectors 356a and 356b are also indicated in FIG. 3B. FIG. 3C shows the intensity distribution of the interferometric pattern shown in FIG. 3B along the horizontal direction (i.e., along the distance of the probe plane).

In operation, when one reflector (e.g., 320) in the system 300 is tilted with respect to the second reflector (e.g., 330), the light reflected from the reflectors 303a and 303b do not follow the coincident paths, thereby projecting an interference pattern on the probe plane as shown in FIG. 3B. This interferometric pattern can be a sinusoid (see, e.g., FIG. 3C) whose frequency and phase varies as a function of the relative position of the two reflectors 320 and 330 as well as the relative tilt. When the moving reflector 330 is translated between positions 330a and 330b, the dark and bright portions of the light translate left or right. By placing two photodiodes 356a and 356b in different locations on this interferometric pattern, two parts of this sinusoidal curve can be measured with a fixed phase delay.

With two signals from the two detectors 356a and 356b, the position and direction of travel can be calculated by using an analog encoder scheme where the phase delay resulting from a tilt angle θ can be found through calibration. Without being bound by any particular theory or mode of operation, the signal at the two photodiodes can be used to calculate the relative position using the following scheme where the two signals at positions 1 and 2 are a(z) and b(z), respectively:

$$a(z) = \cos\left(\frac{2\pi z}{\lambda}\right) \tag{1}$$

$$b(z) = \sin\left(\frac{2\pi z}{\lambda} - \phi\right) = \sin\left(\frac{2\pi z}{\lambda}\right)\cos(\phi) - \cos\left(\frac{2\pi z}{\lambda}\right)\sin(\phi) \tag{2}$$

The phase difference between the two signals can be a function of tilt angle θ and the distance between the two sensors d, $$\phi = -\frac{\pi}{2} + \frac{2\pi}{\lambda}\Delta \tag{3}$$

$$\Delta = d\tan(\theta) \tag{4}$$

In order to solve for the position z, the two measured signals can be divided and the position can be found by taking an inverse tangent:

$$\frac{b(z)}{a(z)} = \tan\left(\frac{2\pi z}{\lambda}\right)\cos(\phi) - \sin(\phi) \quad (5)$$

resulting in the final equation for determining the relative position of the two mirrors, $$z = \frac{\lambda}{2\pi}\tan^{-1}\left(\frac{b(z) + a(z)\sin(\phi)}{a(z)\cos(\phi)}\right) \quad (6)$$

In order to solve this equation, the input data can first be scaled such that the data is between −1 and +1. Then the position can be calculated by using the arctangent function with two arguments, with proper unwrapping of the phase of the output data. The relative phase delay can be calibrated by running a fast ramp on the actuator. Then a Lissajou plot can be made from the two signals and a quick fit can be made to determine the phase delay. This calibration step can take about 2 seconds to complete with the user interface. Because the imaging system and the motor flexure system are relatively stable, the calibration can remain valid for a long time.

Figure 4A:
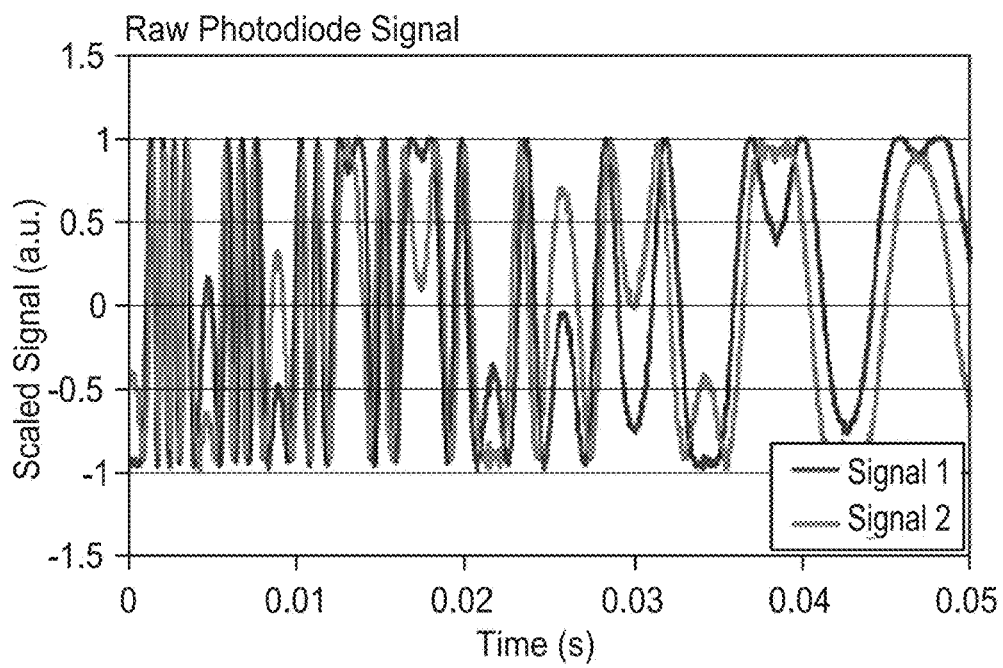
FIG. 4A shows an example of photodiode signals acquired using the system shown in FIG. 3A.
Figure 4B:
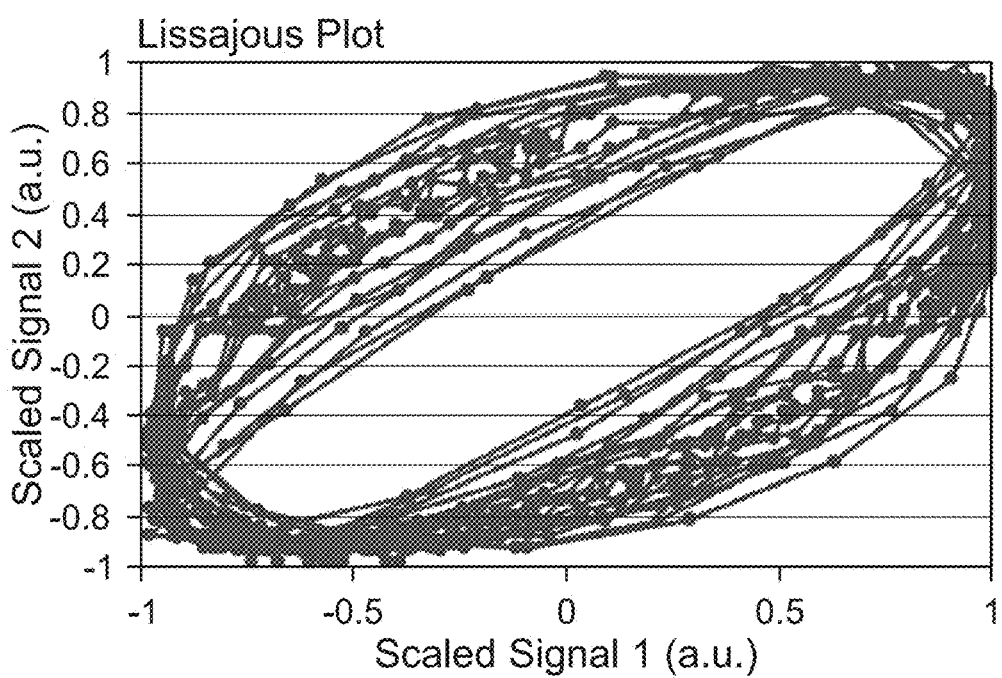
FIG. 4B shows a Lissajous plot of the photodiode signals shown in FIG. 4A.
Figure 4C:
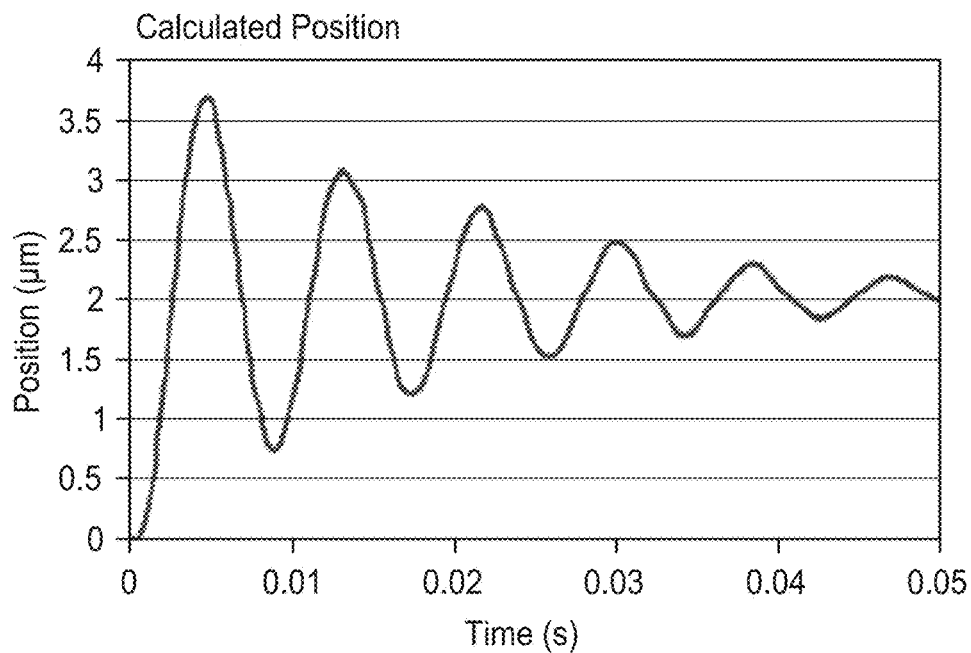
FIGS. 4C and 4D show position and phase change, respectively, of the moving mirror calculated from the data shown in FIGS. 4A and 4B.
Figure 4D:
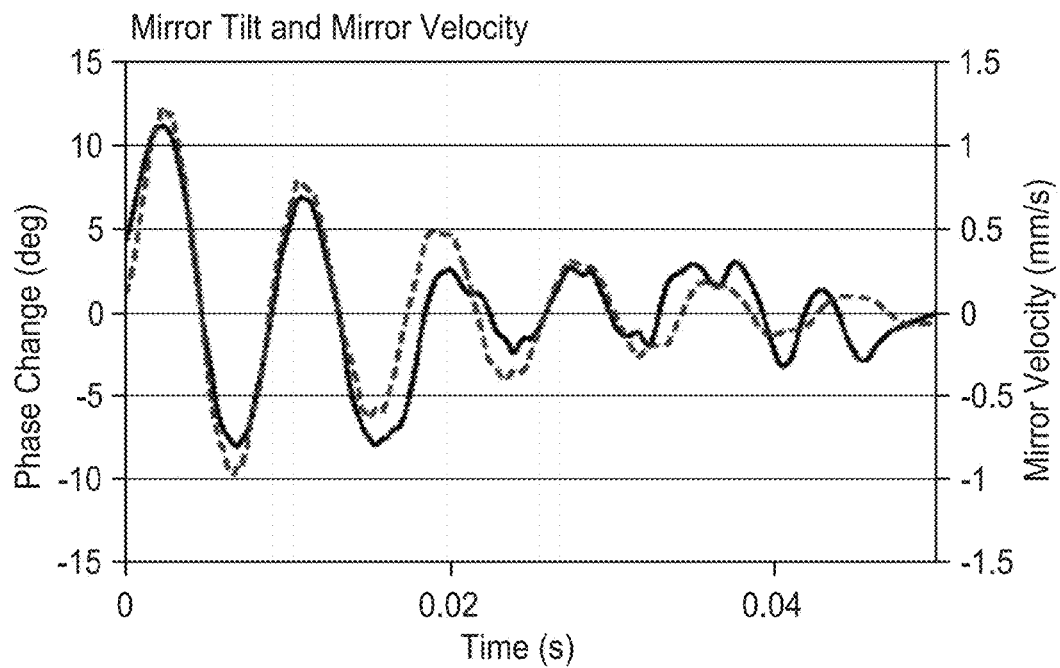

FIGS. 4A-4D show an example set of experimental data using the system 300. FIG. 4A shows photodiode signals acquired by the two detectors 356a and 356b. FIG. 4B shows a Lissajou plot of the photodiode signals shown in FIG. 4A. FIGS. 4C and 4D show the position and phase change of the moving reflector 330 calculated from the photodiode signals shown in FIG. 4A.

Data shown in FIGS. 4A-4D is acquired when a weak cantilever is used to hold the reflector 330, which can cause the reflector 330 to tilt back and forth as a function of the reflector velocity due to drag. Since the trace of the Lissajou plot does not go over itself, this shows that the phase changes over time due to mirror tilt. By calculating the instantaneous phase difference and the velocity of the reflector 330, it is clear that the two signals match up well. This effect disappears when the component holding the reflector 330 is strengthened, thereby changing the Lissajou plot into a perfect oval with a constant phase delay.

The system 300, theoretically, can have infinite positioning resolution. In practice, the positioning resolution can be limited by, for example, the resolution of the analog-to-digital converter (ADC) used to measure its magnitude, as well as the inherent noise in the circuit system and on the photodiodes 356a and 356b (e.g. dark current). The resolution limitation for a single photodiode 356a or 356b can be roughly $\Delta z = \lambda/(2(\Delta V/V_{max})B_{ADC})$, which is a function of the reference wavelength $\lambda$ and the number of bits of the ADC between the signal maximum and signal minimum $(\Delta V/V_{max})B_{ADC}$. The maximum positioning resolution for this wavelength can be approximately 0.1 nm for a 12-bit ADC.

Measurement of Reflector Positions Using Four-Signal Encoders

FIG. 5A shows a schematic of a position measurement system 500 using four-signal encoders. The system 500 includes a beam splitter 510 to receive a probe beam 505 and divide the probe beam 505 into two parts. A first reflector 520 reflects the first part of the probe beam 505 and a second reflector 530 reflects the second part of the probe beam 505. The second reflector 530 can move between two positions 530a and 530b. The two parts of the probe beam 505 after reflections from the corresponding reflector 520 and 530 are combined by the beam splitter 510 and directed to four detectors 556a, 556b, 556c, and 556d, which sense an interference pattern generated by the two parts of the probe beam 505. The four detectors 556a to 556d also define a two-dimensional probe plane.

FIG. 5B shows an example of an interferometric pattern on the probe plane where the four detectors 556a to 556d are placed. The locations of the four detectors 556a to 556d are also indicated in FIG. 5B. FIG. 5C shows the intensity distribution of the interferometric pattern shown in FIG. 5B along two directions. One direction is defined by the two detectors 556a and 556b (e.g., from 556a to 556b), and the other direction is defined by the two detectors 556c and 556d (e.g., from 556c to 556d).

With a two-dimensional probe plane, the interferometric pattern can be tilted and can be projected differently on the four photodiodes 556a to 556d with a relative phase difference in the tip direction and in the tilt direction. The signals on the four sensors can be defined as:

$$a(z) = \cos\left(\frac{2\pi z}{\lambda}\right) \quad (7)$$

$$b(z) = \sin\left(\frac{2\pi z}{\lambda} - \phi_{ab}\right) \quad (8)$$

$$c(z) = \sin\left(\frac{2\pi z}{\lambda} - \phi_{ac}\right) \quad (9)$$

$$d(z) = \sin\left(\frac{2\pi z}{\lambda} - \phi_{ad}\right) \quad (10)$$

The positions calculated by comparing the signals between each of these points are:

$$z_{ab} = \frac{\lambda}{2\pi}\tan^{-1}\left(\frac{b(z) + a(z)\sin(\phi_{ab})}{a(z)\cos(\phi_{ab})}\right) \quad (11)$$

$$z_{ac} = \frac{\lambda}{2\pi}\tan^{-1}\left(\frac{c(z) + a(z)\sin(\phi_{ac})}{a(z)\cos(\phi_{ac})}\right) \quad (12)$$

$$z_{bd} = \frac{\lambda}{2\pi}\tan^{-1}\left(\frac{d(z) + b(z)\sin(\phi_{bd})}{b(z)\cos(\phi_{bd})}\right) \quad (13)$$

$$z_{cd} = \frac{\lambda}{2\pi}\tan^{-1}\left(\frac{d(z) + c(z)\sin(\phi_{cd})}{c(z)\cos(\phi_{cd})}\right) \quad (14)$$

The relative phase angles between the signals are then:

$$\phi_{ab} = -\frac{\pi}{2} + \frac{2\pi}{\lambda}\Delta_x \quad (15)$$

$$\phi_{ac} = -\frac{\pi}{2} + \frac{2\pi}{\lambda}\Delta_y \quad (16)$$

$$\phi_{bd} = -\frac{\pi}{2} + \frac{2\pi}{\lambda}\Delta_y \quad (17)$$

$$\phi_{cd} = -\frac{\pi}{2} + \frac{2\pi}{\lambda}\Delta_x \quad (18)$$

$$\phi_{ad} = -\frac{\pi}{2} + \frac{2\pi}{\lambda}(\Delta_x + \Delta_y) \quad (19)$$

The phase differences are based on the x and y distance between the four sensors as well as the relative tip $\theta_x$ and tilt $\theta_y$ such that:

$$\Delta_x = z_{bd} - z_{ac} = d_x \tan(\theta_x) \quad (20)$$

$$\Delta_y = z_{cd} - z_{ab} = d_y \tan(\theta_y) \quad (21)$$

Other than the interferometric measurement system described above, various other measurements systems can also be used to monitor the position of the moving reflector 130 in the system 100. In one example, a Linear Variable Differential Transformer (LVDT) can be used to measure positions of the moving reflector 130.

In another example, the position of the moving reflector 130 can be monitored by a potentiometer, which can have a wiper contact linked to a mechanical shaft. The shaft can be mechanically coupled to the moving reflector. The movement of the shaft, induced by the movement of the moving reflector, can cause the resistance value between the wiper and the two end connections of the potentiometer to change, thereby providing an electrical signal that is dependent on the position of the shaft.

In yet another example, the moving reflector 130 can be coupled to a confocal sensor to measure its positions. For example, a confocal position sensor can use a polychromatic white light that is focused onto the target surface by a multi-lens optical system. The target surface can be the back surface of the moving reflector 130, the holder of the moving reflector 130, or any other surface that can move together with the moving reflector 130. The multi-lens optical system can disperse the light into monochromatic stages (colors) along the measurement axis. A specific distance to the target can be assigned to each wavelength in a factory calibration. Typically, only the wavelength which is exactly focused on the target is used for the measurement. In other words, detecting the wavelength of the lighted reflected by the target surface can provide distance information of the target surface.

In yet another example, a capacitive displacement sensor can be employed to detect position of the moving reflector 130. For example, the capacitive displacement sensor can include a conductive surface placed near another conductive surface attached to the moving reflector 130. As the moving reflector 130 moves, the capacitance between the two conductive surfaces changes accordingly, thereby providing distance information between the two conductive surfaces.

Piezoelectric Actuators

For linear actuator implementations such as the motor 200 shown in FIGS. 2A-2B, angular misalignment as a function of actuator travel almost always exists. As described above, reconstructing the spectral image using actual positions, instead of desired positions, of the moving reflector in imaging spectrometers can compensate the effects of this misalignment. Nevertheless, using optional piezoelectric actuators can further improve the accuracy of the spectral imaging systems. The piezoelectric actuators can be combined with the motor 200 shown in FIGS. 2A-2B, where the motor 200 provides high stroke and the piezoelectric actuators provide fast dynamics.

Figure 6A:
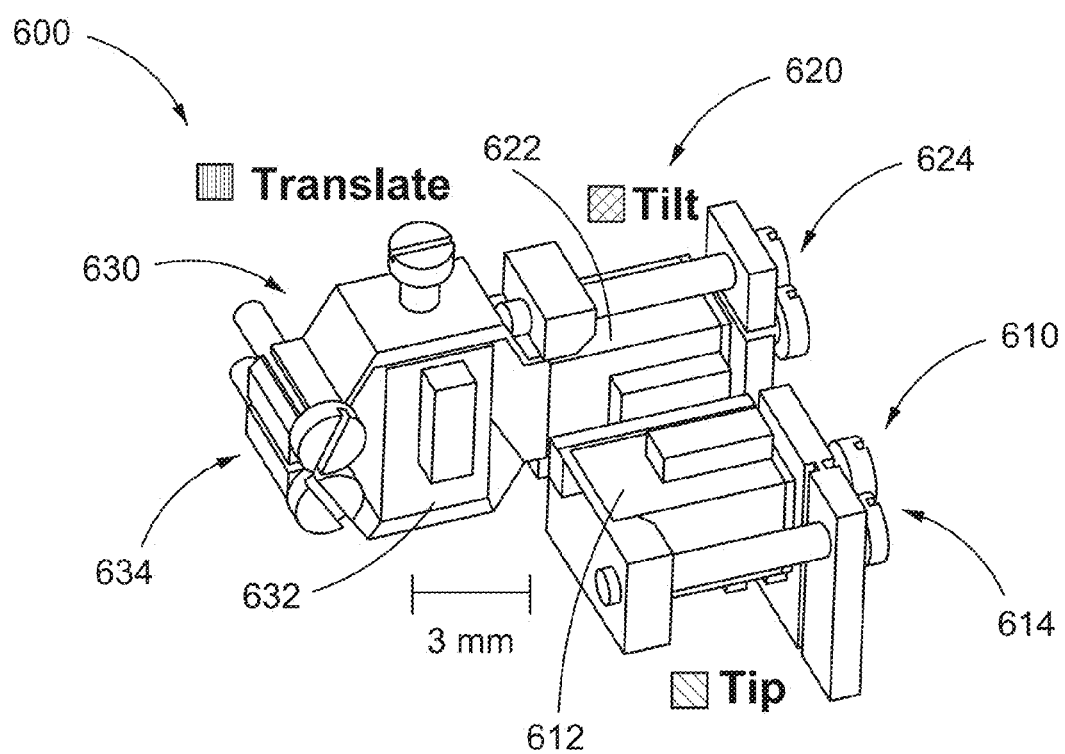
FIGS. 6A-6E show schematics of a multi-axis piezoelectric actuator that can be used to fine tune the moving reflector in the system shown in FIG. 1A.
Figures 6B, 6C:
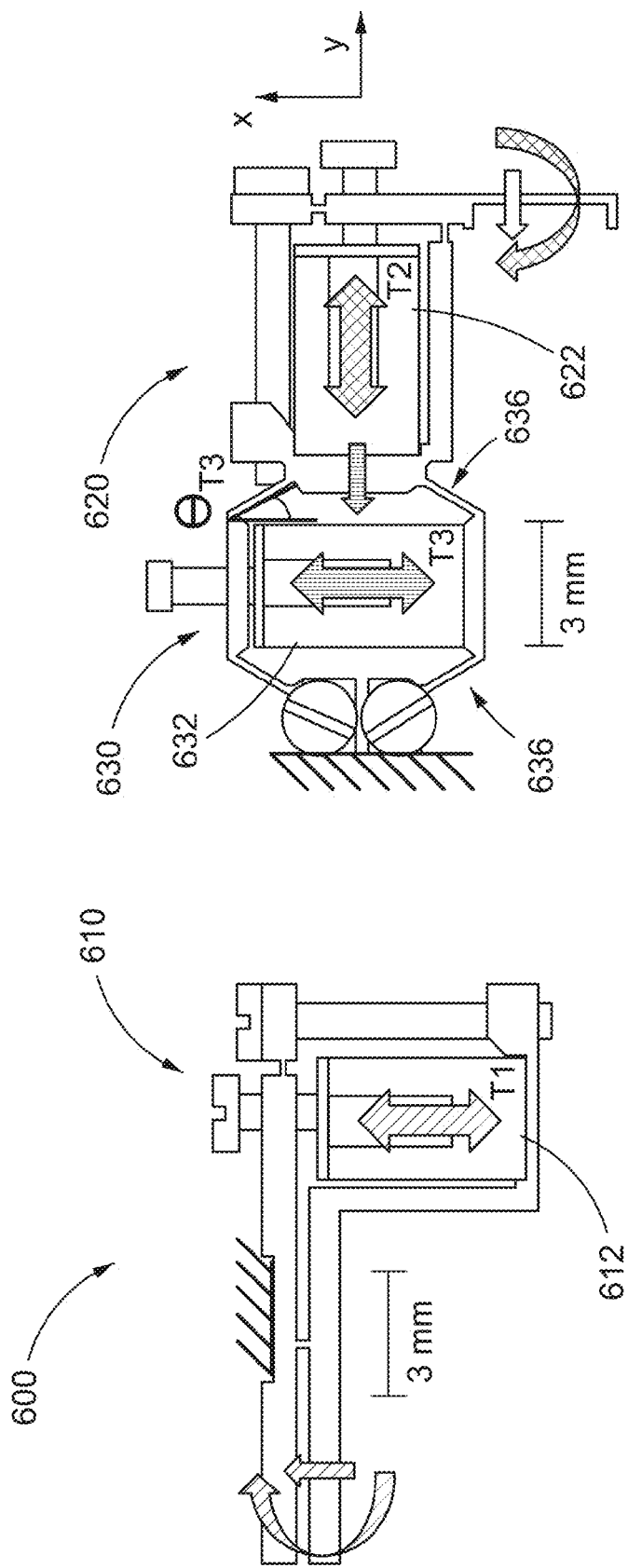

FIGS. 6A-6C show schematics of a piezoelectric actuator 600 that can be used in the imaging system 100 to fine tune the position of the reflector 120 and/or the reflector 130. FIG. 6A shows a perspective view of the actuator 600 and FIGS. 6B-6C show a close-up view of each axis (e.g., translation, tip, and tilt) of the actuator 600. The actuator 600 includes three sub-actuators: a tip sub-actuator 610 to provide tip movement, a tilt subs-actuator 620 to provide tilt movement, and a translation sub-actuator 630 to provide translation movement. Each sub-actuator 610 to 630 is in charge of one degree of freedom. Each sub-actuator 610, 620, and 630 also includes a corresponding piezoelectric material 612, 622, and 632, and two screws 614, 624, and 634. Similarly, the screws 614 in the tip sub-actuator 610 and the screws 624 in the tilt sub-actuator 620 are used to apply a small preload to the sub-actuators and to help change zero point of the alignment. To prevent the screw from damaging the piezoelectric materials 612 and 622, an additional stainless steel plate can be placed at the end of the sub-actuators 610 and 620 to help distribute point loads.

The translation actuator works slightly differently. When it expands, it can force the flexures 636 to stretch and causes a contraction in the orthogonal direction. The screws 634 are used to apply a preload to the piezoelectric material 632. This arrangement can be used to amplify translation and is a function of the angle between the flexure and the piezoelectric actuator $\theta_{T3}$:

$$\frac{\Delta y}{\Delta x} = -\cot(\theta_{T3}) \quad (22)$$

As the piezoelectric actuator expands in the x-direction (indicated in FIG. 6C), the contraction in the y-direction can be a function of the angle. As the angle becomes shallower, the displacement becomes larger. At an angle of about 30 degrees, the contraction can be 1.7 times the expansion of the piezoelectric material 632. In practice, the deformation of other mechanical components may limit the contraction.

Figures 6D, 6E:
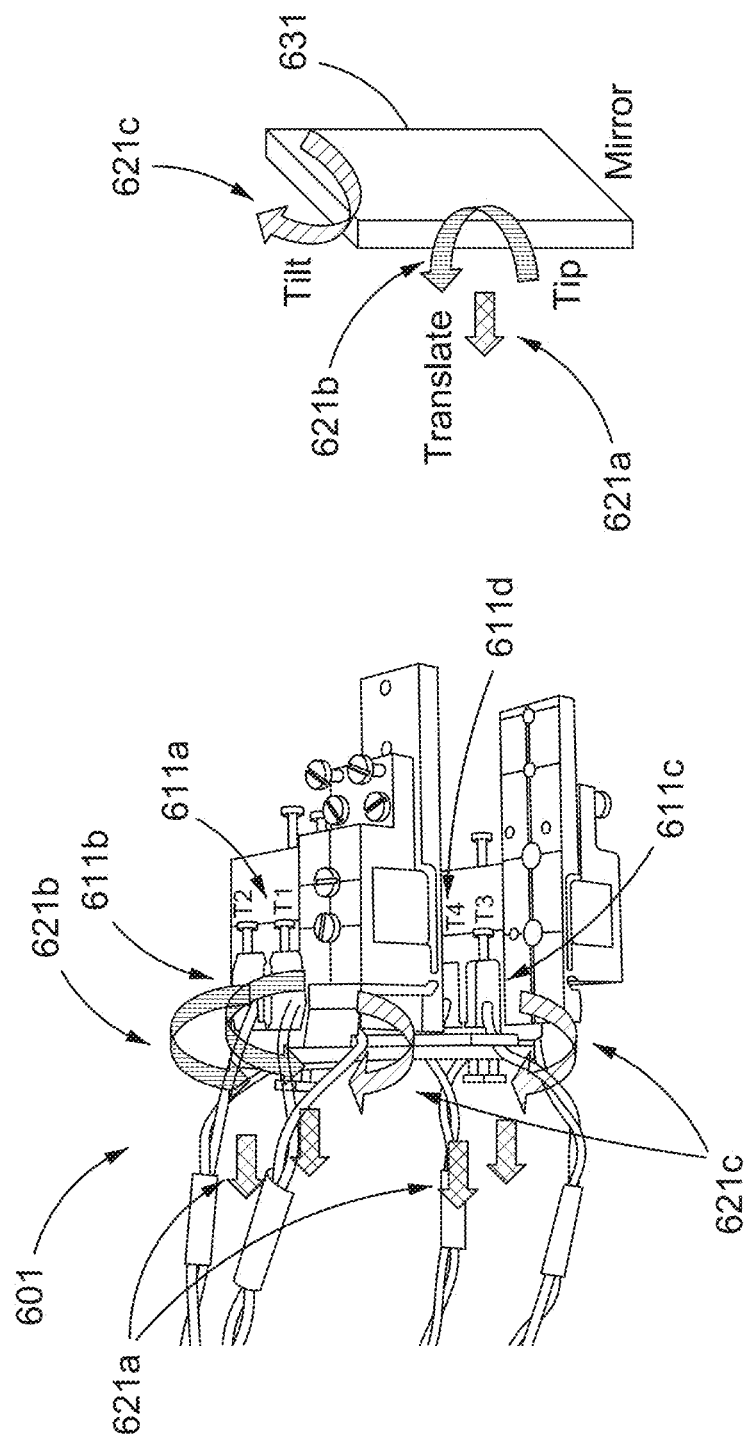

FIGS. 6D and 6E illustrate another piezoelectric actuation system 601 using four actuators 611a, 611b, 611c, and 611d. The four actuators 611a to 611d are disposed in parallel with each other. Motions that can be achieved by the four actuators 611a to 611d include translation 621a, tip 621b, and tilt 621c, as illustrated in FIG. 6D. FIG. 6E also shows a mirror 631 and the corresponding motions including translation 621a, tip 621b, and tilt 621c. Parallel actuators can achieve higher bandwidths due to increased system stiffness between the piezoelectric actuators 611a to 611d and the location of the mirror 631. Here, four piezoelectric actuators 611a to 611d act together to move the mirror 631. If all four piezoelectric actuators 611a to 611d expand, then the mirror 631 translates. If only the top two actuators 611a and 611b or the bottom two actuators 611c and 611d expand, then the mirror 631 tips. If only the left two actuators 611a and 611c or the right two actuators 611b and 611d expand, then the mirror 631 tilts. The actuation system 601 also allows for both positive and negative tip and tilt and does not require a preload force or preload voltage for those motions.

Methods of Spectral Imaging Using Actual Positions of the Moving Reflector

Figure 7:
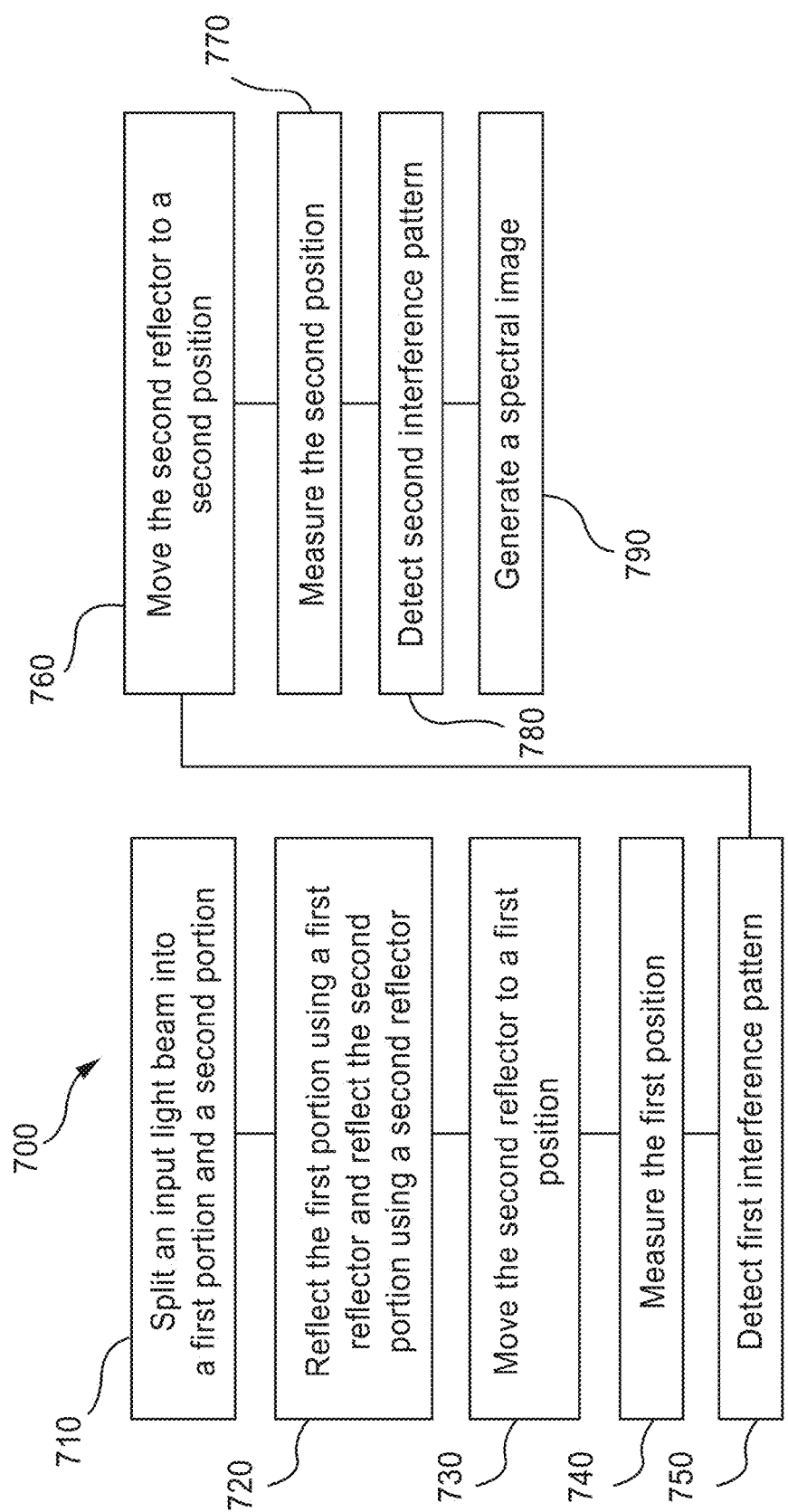
FIG. 7 illustrates a method of spectral imaging using actual positions of the moving reflector for image reconstruction.

FIG. 7 illustrates a method 700 of spectral imaging using actual locations of the moving reflector. At step 710 of the method 700, a splitter can split an input light beam, which can be reflected, scattered, or emitted by an object to be imaged, into two portions: a first portion and a second portion. A first reflector then reflects the first portion of the input light beam and a second reflector reflects the second portion of the input light beam, at step 720. The first portion and the second portion of the input light beam, after reflection by the corresponding reflector, can interact at a detector plane to form an interference pattern (also referred to as an autocorrelation).

At step 730 of the method 700, the second reflector is moved to a first position (e.g., using an actuator), which is measured at step 740. A detector then detects a first interference pattern, at step 750, when the second reflector is at the first position. Similarly, at step 760 of the method 700, an actuator can move the second reflector to a second position, which is measured at step 770. The detector then detects a second interference pattern, at step 780, when the second reflector is at the second position. The loop of moving the second reflector, measuring the position of the second reflector, and acquiring autocorrelation can be repeated many times until a sufficient number of autocorrelations are acquired for image reconstruction at step 790. The reconstruction of the spectral image uses the acquired autocorrelations as well as the measured actual positions of the second reflector.

Figure 8A:
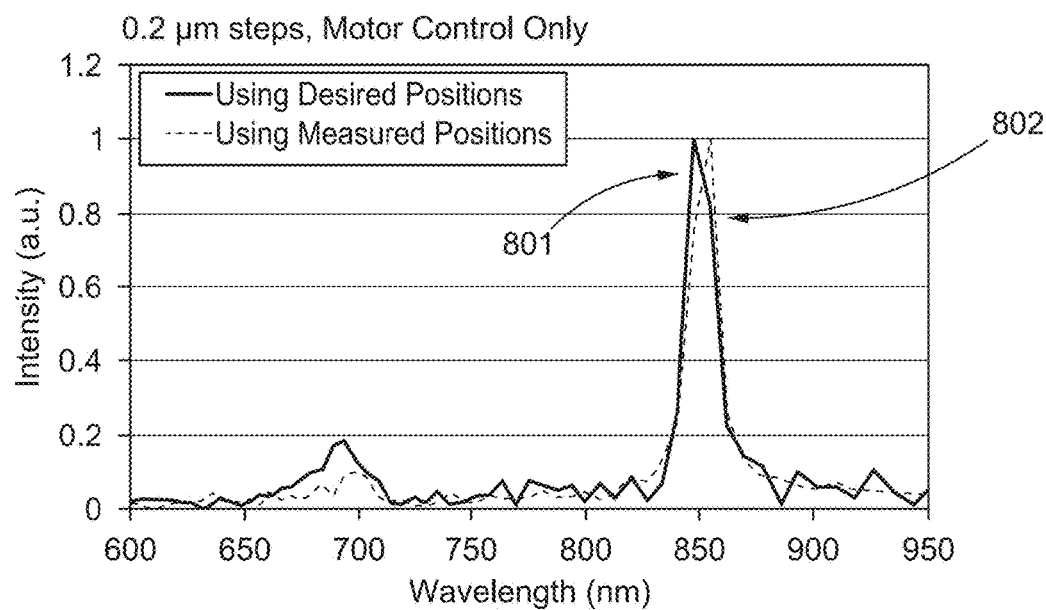
FIGS. 8A-8D show experimental results of reconstructed spectral images using desired positions and actual positions of the moving reflector in an imaging spectrometer.

FIGS. 8A-8D show experimental results of spectral imaging using actual positions of the moving reflector for reconstruction. The data is taken at a frame rate of 2010 fps. FIG. 8A shows the reconstructed spectral images when data is taken at a step size of 0.2 μm and the moving reflector is controlled by only a motor. Spectrum 801 is reconstructed using desired positions of the moving reflector, while spectrum 802 is reconstructed using measured positions of the moving reflector.

Figure 8B:
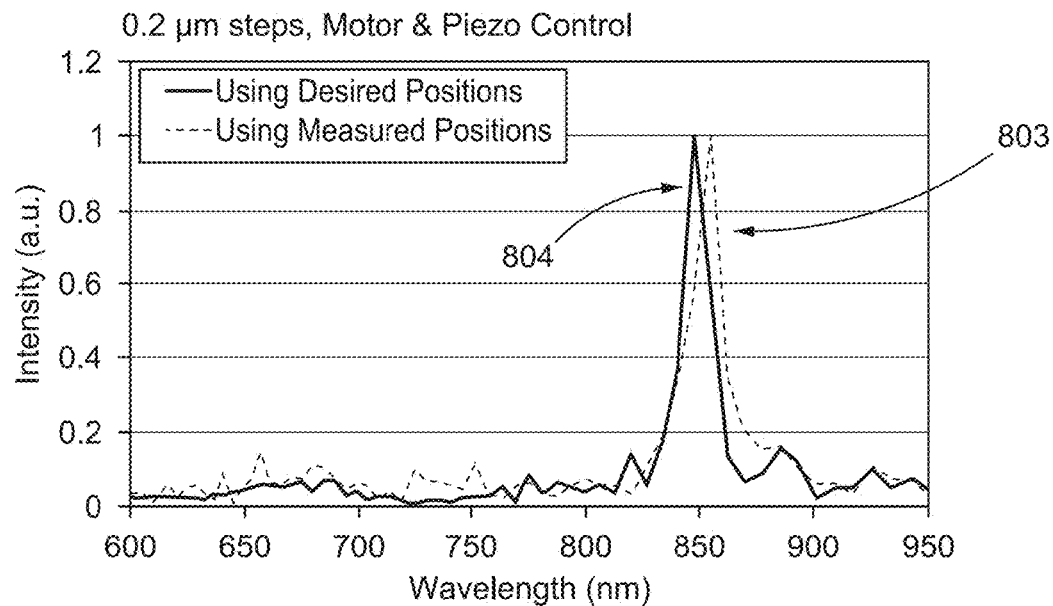

FIG. 8B shows the reconstructed spectral images when data is taken at a step size of 0.2 μm and the moving reflector is controlled by a motor and a piezoelectric actuator. Spectrum 803 is reconstructed using desired positions of the moving reflector, while spectrum 804 is reconstructed using measured positions of the moving reflector.

Figure 8C:
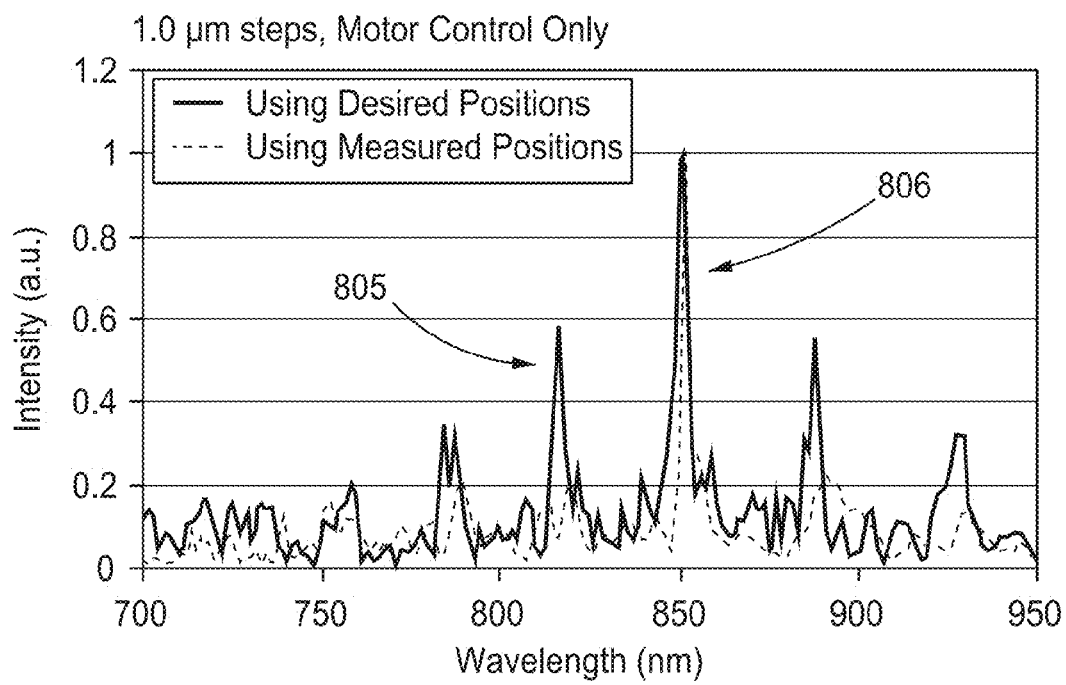

FIG. 8C shows the reconstructed spectral images when data is taken at a step size of 1 μm and the moving reflector is controlled by a motor only. Spectrum 805 is reconstructed using desired positions of the moving reflector, while spectrum 806 is reconstructed using measured positions of the moving reflector.

Figure 8D:
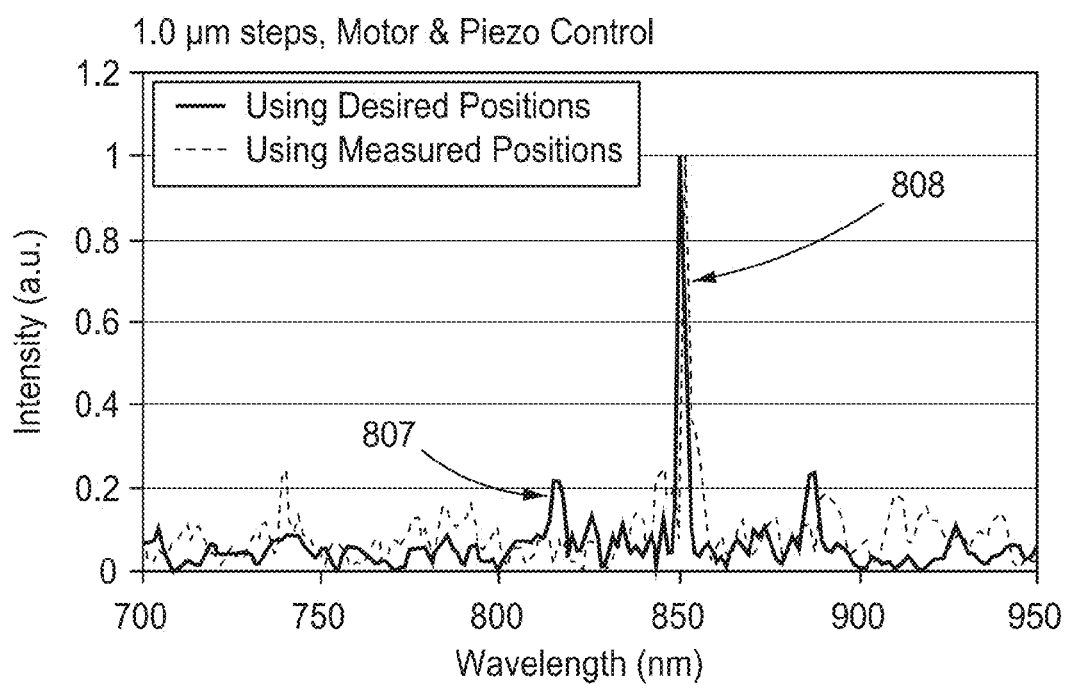

FIG. 8D shows the reconstructed spectral images when data is taken at a step size of 1 μm and the moving reflector is controlled by a motor and a piezoelectric actuator. Spectrum 807 is reconstructed using desired positions of the moving reflector, while spectrum 808 is reconstructed using measured positions of the moving reflector.

FIGS. 8A-8D show that at step sizes of 1.0 μm, the motor-only control method produces extra peaks in the data that are not present when hybrid control (motor and piezoelectric actuator) is used. The extra peaks in the data can be eliminated by calculating the Fourier transforms using the measured positions rather than using the equally spaced desired positions. Since the motor only controller may not accurately position the mirror at 2010 fps, the measured position and desired positions are very different. By using a least squares solver or any other solver (e.g., an adaptive sampling method, and an iterative sampling method) that is capable of incorporating the sampling location, the error due to positioning inaccuracies can be removed.

The method 700 illustrated in FIG. 7 can also be useful in developing small imaging spectrometers for handheld applications, where either the spectrometer or the source being tested may be held by a human. Humans are not good at maintaining accurate positions and are a source of vibrations. Therefore, it is helpful to consider the effects of disturbances caused by humans on the measurement accuracy.

Conventional methods to address human disturbances include image tracking (e.g., edge tracking) and machine vision methods. However, there is a challenge in using these methods for spectral imaging because the edges of interferograms tend to move from image to image for some experiments. For situations where there is no tilt, the image brightness can instead change from image to image.

Alternative methods for image tracking can be used for these cases. One approach to the problem can be sampling at a rate that is significantly faster than the rate of human motion. For example, if only 10 frames are required to make the spectral image with the desired spectral resolution and if the human motion was on the order of 5 Hz, it is possible to sample at 2000 fps and obtain all the desired images in 5 ms. This is much faster than frequency of the human motion so the objects of interest may not have moved much from frame to frame. By sampling quickly, human motion disturbances can be rejected. In addition, the blur from human motion can be removed if the sampling is faster. In order to push the limits of the sampling rate, the approached used in the method 700 can be utilized to obtain accurate spectra at speeds that may be beyond the capabilities of the actuator.

Irregular Sampling

In spectral imaging techniques, the Fourier transform can be used to convert interference patterns into spectra. This transform, however, has many limitations. First the data is usually sampled at evenly spaced intervals at the Nyquist frequency, which usually means a large number of samples are taken to generate a spectral image. For example, if a 5 nm resolution at $\lambda_0$=850 nm is desired, over 700 samples would be taken. If the camera is sampling at 30 frames per second, gathering a full hyperspectral image may take up to 23 seconds. Even for a high-speed camera at 2000 frames per second, a video rate spectrum may not be achieved. This is a clear limitation of Fourier transform methods that utilize traditional uniform sampling at the Nyquist frequency.

In order to reduce the sampling rate while maintaining the desired resolution, a variety of irregular sampling methods can be used. Examples of irregular sampling techniques include under-sampling, non-uniform sampling, optimal sampling, adaptive sampling, and recursive update techniques. These methods can be used in conjunction with advanced solution methods other than the fast Fourier transform (FFT) or the discrete Fourier transform (DFT). The advanced solution methods include techniques like the L1 or L2 (least squares) techniques or fast digital filtering methods for real-time custom color filtering.

Generalized Solution

The solution method presented here can be derived from fast orthogonalization techniques used for sampling Fourier transform data and for solving Volterra kernels. The general solution for any sampling method can be obtained from setting up the problem in an equation of the form:

$$y(n)=\Sigma_{m=1}^{M} A_m P_m(n)+e(n) \qquad (23)$$

with matrix form Y=PA+E, where $P_1(n)=1$, $P_{2i}(n)=\cos(\omega_i z(n)/c)$, $P_{2i+1}(n)=\sin(\omega_i z(n)/c)$.

Here y(n) is the intensity of the interferometric pattern acquired by the detector (e.g., detector 160 shown in FIG. 1A) while the moving reflector 130 is at location z(n), e(n) is the error and $A_m$ contains the spectral information (i.e., the coefficient for spectral component at wavelength $\lambda_m$). The matrix $P_m$ is constructed from real trigonometric polynomials and contains the guesses for different frequencies $\omega_i$ and the locations where measurements are taken z. To convert frequencies to wavelengths, the equation $\lambda_i=2\pi v/(\omega_i)$ can be used, where $v=c/n_1$ is the refractive index of the material propagating the input light beam.

Note that equation (23) is a Hartley transform and not a Fourier transform as all constants are real. Also note that there is no restriction on sampling interval thereby allowing non-uniform sampling. Many possible ways can be used to solve equation (23) and derive the spectral information contained in $A_m$. For example, an $L_2$ norm solution, also known as least square (LS) method can be used, in which case:

$$\hat{A}=(P^TP)^{-1}P^TY \quad (24)$$

Once the solution A is acquired, the results can be mapped back to a magnitude and phase so as to reconstruct a spectral image:

$$J_i=\sqrt{A_{2i}^2+A_{2i+1}^2} \quad (25)$$

$$\zeta_i=\tan^{-1}(A_{2i+1}/A_{2i}) \quad (26)$$

Note that there is no restriction on sampling interval thereby allowing non-uniform sampling and under-sampling. The flexible form of the matrix P allows for any choice of desired frequencies, even no-continuous groups of frequencies indicating many different sets of spectral limits, thereby enabling adaptive sampling. This matrix form can also be used for recursive update algorithms.

Because the true relative phase content of the input light is not preserved in an interferometric measurement, it is therefore not necessary to preserve the phase content in the transform. The phase information can therefore be ignored. The magnitude information can map directly to the spectrum of the measurement. If the amount of data acquired is more than twice the number of wavelengths present in the data (and wavelengths queried), then the $L_2$ algorithm can be used. If the data are sparse, and the amount of data acquired is less than twice the number of wavelengths queried, then an $L_1$ method or an adaptive or iterative $L_2$ algorithm can be used.

Non-Baseband Sampling Methods

In traditional Fourier transform sampling methods, the sampling is usually half the spacing of the lowest wavelength of interest in order to avoid aliasing (Nyquist sampling $\lambda_{min}$ 2$\Delta$z), the maximum wavelength is equal to the sampling range $\lambda_{max}=N\Delta z$, and the number of samples obtained at this spacing determines the resolution of the spectrum. The wavenumber (generally presented in units of cm$^{-1}$), which is the inverse of the wavelength $\upsilon=1/\lambda$, can be used to determine the resolution of the spectrum:

$$\Delta v = \frac{1}{z_{max} - z_{min}} \approx \frac{\Delta\lambda}{\lambda^2} \quad (27)$$

If the sampling is equally spaced, then $\Delta\upsilon=1/(N\Delta z)$ is also true. The wavelength resolution is approximately $\Delta\lambda\approx\lambda^2/(N\Delta z)$ at any given wavelength $\lambda$. This wavelength range with this resolution can be defined as baseband sampling.

By looking at these equations, it is clear that resolution is driven only by the range of sampling. Therefore, it may be possible to ignore the Nyquist sampling limit to achieve a desired wavelength resolution by under-sampling the spectrum if the incoming light is limited only to a certain band of wavelengths. For example, if silicon-based photodiodes are used, the wavelengths can be limited to between about 300 nm and about 1100 nm.

If the band limits $\lambda_{max}$ and $\lambda_{min}$ are known, then the Shannon non-baseband sampling rate can be:

$$\Delta z = \frac{1}{2}\lambda_{min}\left[\frac{\lambda_{max}}{\lambda_{max}-\lambda_{min}}\right] \quad (28)$$

The brackets in this equation indicate taking the integer floor value of the ratio inside the brackets. By utilizing the known band limits of the spectrum, the number of samples for reconstructing the spectrum can be reduced by three to five times, thereby increasing the sampling speed.

Under-sampling or non-baseband sampling is a technique where the sampling interval is larger than the Nyquist sampling interval. Traditionally, this type of sampling is discouraged because it tends to cause aliased data to fold into un-aliased data. However, if the band limits of the system are known, it is possible to prevent folding and use the aliased data directly. This technique can dramatically cut down on the number of data points and can dramatically increase the spectra update rate.

Another method that can be used with known band limits is the optical under-sampling method. Because of trade-off in terms of speed and noise, a cost function can be created to determine the optimal under-sampling interval for a given weight of importance of noise relative to sampling and computation time. For example, the system can be restricted to a constant spectral resolution with a constant set of desired spectral points. An optimal under-sampling interval can be determined using a cost function where the noise ratio $f(\Delta z)$, data acquisition time $g(\Delta z)$, and solution time $h(\Delta z)$ are considered with relative scaling constants $K_1$, $K_2$ and $K_3$, respectively. The sampling interval region can be restricted by the Nyquist sampling rate, the maximum possible sampling step size, the maximum allowable sampling time, and the maximum allowable signal to noise ratio:

$$\arg\min_{\Delta z} K_1 f(\Delta z) + K_2 g(\Delta z) + K_3 h(\Delta z) \quad (29)$$

subject to $$\Delta z \in [\max(\Delta z_{Nyquist}, T_{max}), \min(\Delta z_{Shannon}, SNR_{max})].$$

Adaptive Under-Sampling

In many cases, nothing is known about the spectra before the data are obtained. In this case, it is possible to slowly learn more and more about the spectrum as the data is acquired and adapt the sampling intervals as more information is obtained. Adaptive under-sampling takes advantage of the fact that the act of obtaining more data points in the spectra automatically yields more spectral data. Since there is more information about the underlying spectrum, it is then possible to tailor the input to converge on the optimal, wider sampling interval over a single sampling sweep, thereby producing the desired spectral resolution faster.

For example, a controller implementing adaptive sampling may slowly increase the sampling interval as it learns more about the underlying spectra. Existing adaptive sampling methods are typically purely mathematical solution techniques and do not provide direction on how the data should be adaptively sampled. The spectral data obtained from imaging Fourier transform spectra presents a unique case where the true underlying spectrum is fixed for a given sample and can be sampled adaptively at any desired position at any time. In addition, the spectra can have incoherent or broadband data concentrated at the center of the interferometer alignment, which is treated differently than the narrowband data. These factors lead to a unique adaptive under-sampling algorithm that can be effectively implemented for imaging Fourier transform spectrometers.

Figure 9:
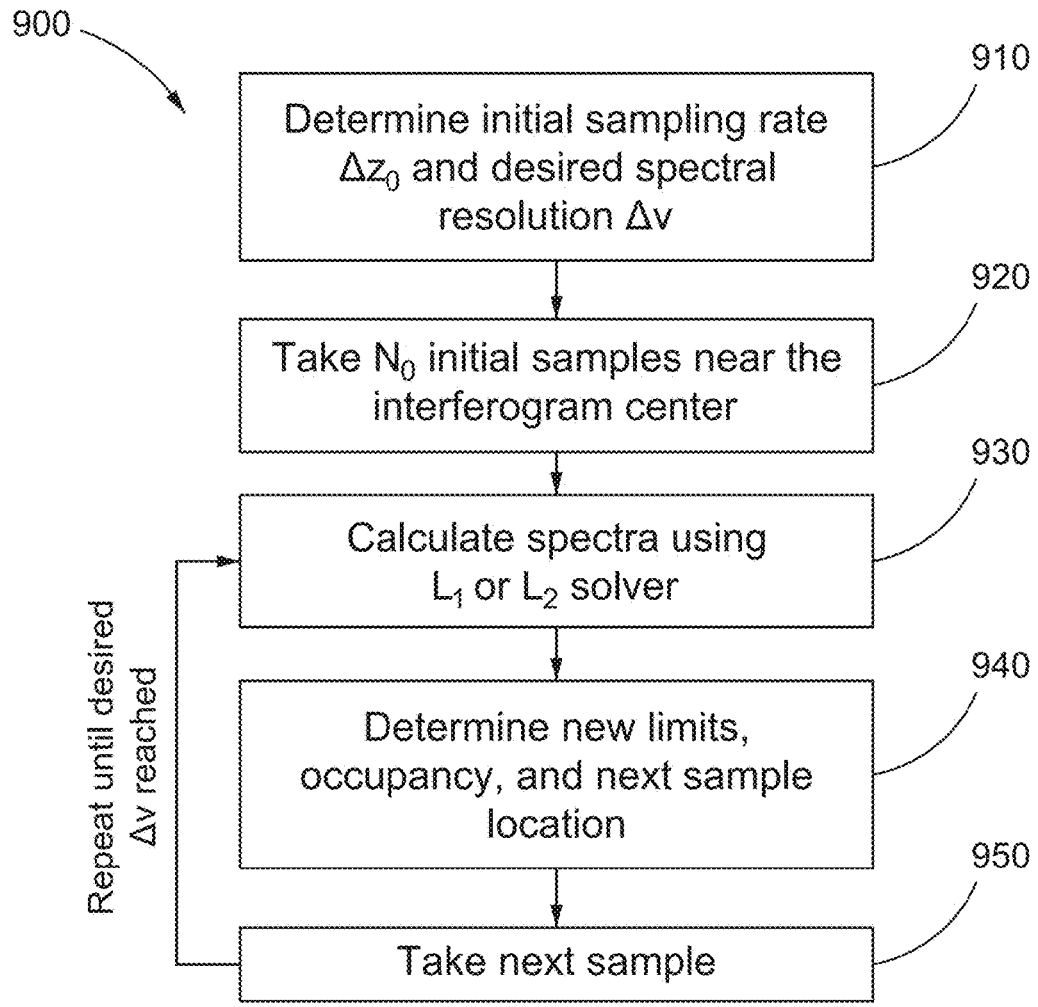
FIG. 9 illustrates a method of adaptive sampling.

FIG. 9 illustrates a method 900 of adaptive sampling that can be executed by a controller or other processor of or coupled to a spectral imaging device. At the first step 910, a user determines the desired resolution and initial sampling rate, which is related to the known band limits $\lambda_{max}$ and $\lambda_{min}$:

$$\Delta z_0 = \frac{1}{2}\lambda_{min}\left[\frac{\lambda_{max}}{\lambda_{max} - \lambda_{min}}\right] \quad (30)$$

where $z_i = z_{i-1} + \Delta z_0$.

Then a small number of initial samples No are collected near the interferogram center at step 920 of the method 900. Once this is completed, the low-resolution spectra is calculated, at step 930, using the generalized solver. Using the small number of initial samples can also force the system to sample the center of the interferogram more heavily, thereby capturing more of the broadband spectral data.

When this result is obtained, the controller proceeds to step 940, where the limits (locations in the spectra where information exists and the value is above $\delta_L$) can be determined, thereby allowing the calculation of the occupancy (ratio of occupied to total spectral data points). Determining the occupancy in turn allows the selection of the next sampling step with some relaxation term R≥1 and an occupancy $\Gamma_i = N_{occupiedi}/N_{totali}$ where, $$\overline{\Delta z} \leq \frac{1}{2}\lambda_{min}\frac{R}{\Gamma_i}\left[\frac{\lambda_{max}}{\lambda_{max} - \lambda_{min}}\right] \quad (31)$$

And $z_i = z_{i-1} + \Delta z_i$.

Once some samples are taken, the method proceeds to step 950, where the spectra are recalculated using the method outlined above and the procedures are repeated until the desired resolution is achieved. Note here that an $L_2$ norm algorithm requires that the limits become smaller (only occupied parts of the spectra are set up in the calculation of $\omega_i$) because there would otherwise not be enough data to solve the problem. An L1 norm algorithm would not have such a restriction but would run much slower. The shrinking limits in the algorithm make the L2 norm solution feasible. In addition, the controller can continue until the limits stop changing or at some predefined number of iterations. The controller can then switch to constant sampling at the maximum interval until the final desired resolution is reached.

Recursive Spectral Update

For many applications, it can be desirable to do continuous spectral sampling. When the spectrum of the image changes slightly during the acquisition process, it may not be desirable to completely resample the spectra. Instead, old data points from the interferogram can be forgotten and replaced with information from new data points. This allows a gradual adaptation or recursive updating of the calculated spectra and gives the user intermediate information about the system.

While adaptive sampling reduces the number of images necessary to produce a full spectral image, recursive sampling can be used to update the spectral information between full spectral images. For example, if 500 images taken at 2000 frames per second are used to create a single full spectral image, the full spectral image rate can be 4 full spectra per second. If the controller/processor uses a recursive sampling algorithm, it can make small updates to the spectral image after each image. This allows the recursively sampled full spectral image rate to be as high as 40 (update group size of 50) up to 2000 (update group size of 1) frames per second. This can be useful for pushing the spectral update to the user at faster rates. Possible applications include video monitoring of changes in biological fluorescence to events during chemical mixing causing changes in the Raman spectra. Alterations in blood oxygen content of an entire image as a function of heart rate could also be monitored.

Digital Filtering

Unlike other methods that attempt to improve sampling speed or update rates, the digital filtering methods presented in this section attempt to create color images from the "black and white" data obtained from the spectrometer in a fast and effective manner that does not require taking a full FFT or solving the LS equations. The digital filtering method uses a lower (minimal) number of simple calculations per pixel and tracks motions at video rates while reproducing color images from the black and white data. Examples of applications include tracking different fluorescent peaks, tracking different Raman peaks while collecting a minimal amount of data, and simply converting data from a black and white camera to color without the use of Bayer masks or rotating filter disks.

The digital filter methods described herein can create color images from any set of wavelength bands and can assign as many colors to as many wavelength bands as desired. In general, broadband colors, similar to the Bayer filters in traditional color cameras, can be relatively quick and easy to reproduce from interferometric data because those filters are so broad that only a few terms are needed to create a filter for those wavelengths. It can be more challenging when there are narrowband colors, such as two laser wavelengths that are very close together and a third that is further away.

Figure 10:
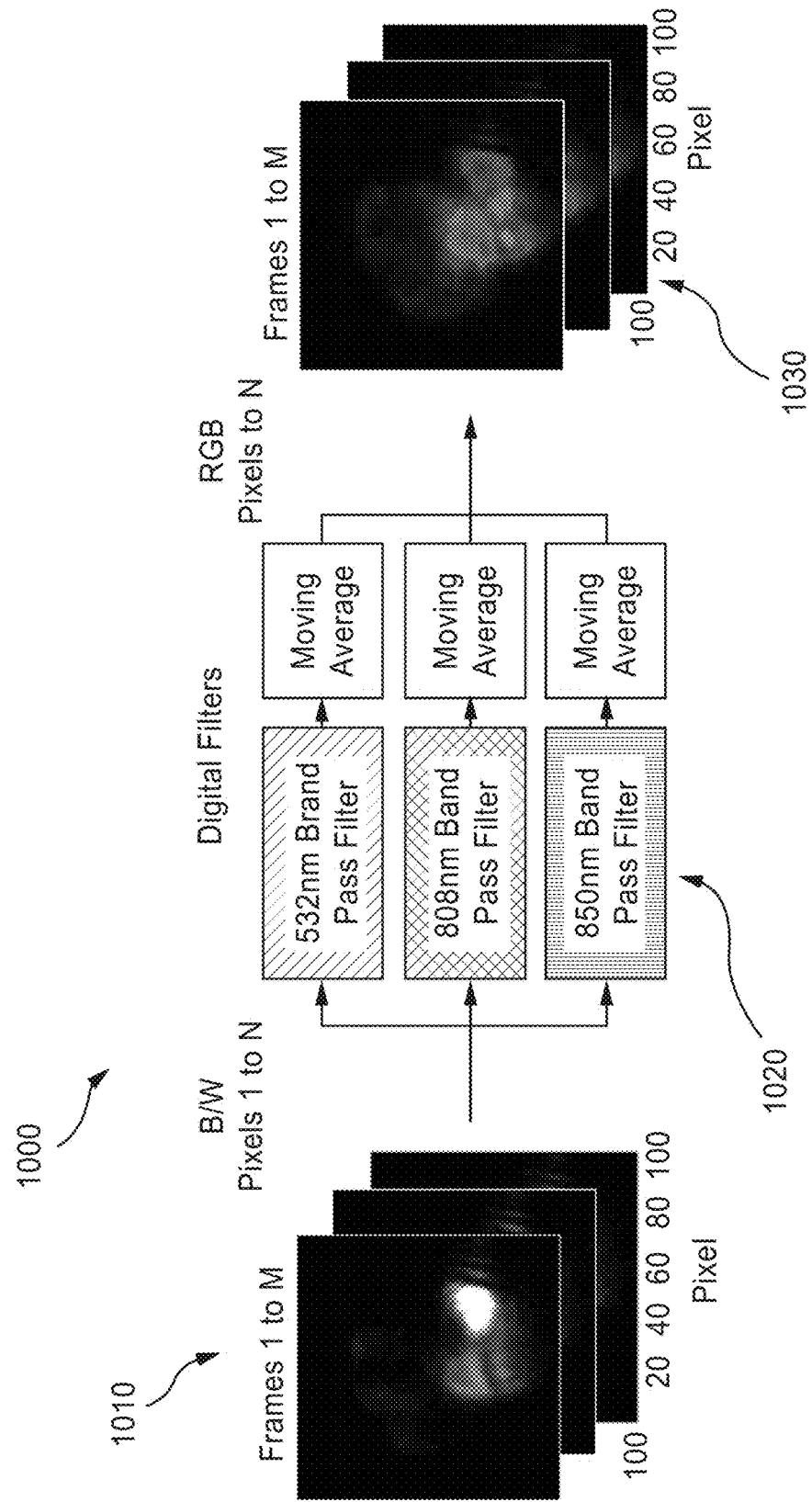
FIG. 10 illustrates a method of digital filtering to create color images from black-and-white raw images.

FIG. 10 illustrates a method 1000 of digital filtering and creating color images from black-and-white images. This method can be performed by suitably programmed or operated versions of the spectral imaging device described above. At step 1010 of the method 1000, a processor/controller acquires black-and-white images (the total number of images is denoted as M). Light beams that create these black-and-white images (also referred to as raw images) can include three spectral components: one at 532 nm, another at 808 nm, and a third component at 850 nm. Once the raw images are obtained, a filter receives each raw image and splits the image into different pixels. Each pixel is passed through three different bandpass filters that cover distinct wavelength ranges, at step 1020. The output of the filter is then sent to a moving average filter and the resulting data can be reconstructed into a color image, at step 1030. A series of black-and-white images with interferometric data therefore can become a series of color images through this process.

At least two types of filters can be used here: one filter includes uniform sampling and the other filter includes non-uniform sampling. There are two major classes of digital filters, infinite impulse response (IIR) filters and finite impulse response (FIR) filters. The following sections teach how different filters can be designed so that black and white video can be converted to color video in real time with some fixed delay. To design the high pass, low pass, or bandpass filters, the wavelengths of interest and the bandwidths of those wavelengths are required. To reduce ambiguity between different filters for different colors, the overlap of multiple filters should be minimized. Once the filters for a particular sampling scheme (either uniform or non-uniform) are obtained, the digital filter plus the moving average step can be used on each pixel of the black and white video to determine the intensity for each wavelength of interest. This can be combined to form the color video.

Uniform Sampling

Digital filters, in this case, work on time series data. For example, a very simple digital filter could take an average of two data points (intensity levels on one pixel at two different times) at samples n and n−1 to produce an output for sample n. An IIR filter works by considering the data from both the input data (raw pixel intensities at different time steps) and the previously created output data from the previous time steps. This is then used to create a new output for the current time step.

With being bound by any particular theory or mode of operation, an IIR filter has a transmission function of the form:

$$y(n) = \frac{1}{a_0}\sum_{i=0}^{Q_b} b_i x(n-i) - \sum_{j=1}^{Q_a} b_j y(n-j) \tag{32}$$

with both feed-forward filter coefficients $b_i$ and feedback filter coefficients $a_j$. Generally, fewer terms are necessary in the IIR domain than in the FIR domain for similar filter cutoffs due to the feedback terms. These IIR filters can be generally more difficult to convert from any time-domain design using a bilinear transform or Tustin transform and are much more straightforward to design directly in the digital domain.

In one example, a digital IIR filter based on an analog Butterworth filter can be designed for the wavelength at 532 nm because it is sufficiently far away from the other two wavelengths. Elliptical filters can be designed for the 808 nm and 850 nm filters. Elliptical filters usually have sharper cutoffs for the same filter order but have more ripples. The wider the filter in frequency space, the less delay there is in time. For this reason, the edges of the red and green filters can be used to separate the 808 nm from the 850 nm while allowing the filters to be fairly wide overall. In general, these filters can track motions up to about 40 fps when video is taken at 2010 fps.

An FIR filter works by considering only the input data (raw pixel intensities at different time steps) in the creation of the output for the current time step. FIR filters generally use more computations for the similar filter cutoff characteristics but they can have a constant delay equal to half their filter order. For FIR filters, the order is $Q_b$. FIR filters are also easier to generate from continuous domain filter designs. An FIR filter has the form:

$$y(n)=\Sigma_{i=0}^{Q_b} b_i x(n-i) \tag{33}$$

In one example, the red and green filters can be very narrow and have an order of $Q_b$=100 samples (delay of 50 samples). The blue filter can be much broader and has an order of 30 (delay of 15). Because these filters normally do not have a flat region, it can be challenging to use just the edges of the filter to separate the two wavelengths as with the IIR filter. For this same reason, the rejection ratio of the green filter for information at 850 nm and the red filter for information at 808 nm can be potentially lower for the FIR designs.

Non-Uniform IIR Digital Filtering

Filters with the ability to handle non-uniform spacing can be used to correct for those small positioning errors and can be further used for other applications with non-uniform sampling, such as adaptive sampling or random sampling schemes. One example of such filter can be IIR filter. To create a non-uniform sampling IIR filter, a consistent master design can be created in the continuous domain and converted to the digital domain. The more accurate conversion processes may use a Tustin transform, which involves a matrix inversion, although there are some other approximations that are slightly more efficient.

A continuous domain filter design in state space form can be converted to the digital domain. Here, the input vector is x(z), the output vector is y(z), the state variable is w(z) and they are all a function of position z:

$$\frac{dw(z)}{dz} = A_d w(z) + B_d x(z) \tag{34}$$

$$y(z) = C_d w(z) + D_d x(z) \tag{35}$$

There are several possible approximations that can be made. The first is an Euler approximation, $$w_n = (I+\Delta z_n A_d)w_{n-1} + B_d \Delta z_n x_{n-1} \tag{36}$$

$$y_n = C_d w_n + D_d x_n \tag{37}$$

The second type of approximation is the bilinear approximation or Tustin transform:

$$\frac{w_n - w_{n-1}}{\Delta z_n} = A_d \frac{w_n + w_{n-1}}{2} + B_d \frac{x_n + x_{n-1}}{2} \tag{38}$$

which has a solution of the form:

$$w_n = \tag{39}$$
$$\left(I - \frac{\Delta z_n}{2}A_d\right)^{-1}\left(I + \frac{\Delta z_n}{2}A_d\right)w_{n-1} + \frac{1}{2}\Delta z_n\left(I - \frac{\Delta z_n}{2}A_d\right)^{-1}B_d(x_n + x_{n-1})$$

$$y_n = C_d w_n + D_d x_n \tag{40}$$

Non-Uniform FIR Digital Filtering

One benefit of using FIR filter designs for non-uniform sampling filter designs is that FIR models translate easily from continuous domain designs. After creating a continuous domain filter, it is possible to simply resample the filter at different points corresponding to the non-uniform sampling points. From a time-domain or frequency domain master filter (with all windowing removed), two vectors can be generated. The first vector can be the master filter and the second vector can be the associated uniformly sampling space vector. In general, the master filter can be oversampled slightly to improve resampling accuracy later. For uniform spacing, the master filter vector is:

$$b_i = b_i^m \Delta z \tag{41}$$

The non-uniform filter can be slightly more complex. Because the sampling is non-uniform, it can be desirable for the filter to have the same non-uniform spacing as the sampling. If the sampling position vector is known then:

$$b_i = b_i^m \Delta z_i \text{ or } b_i = \frac{b_i^m + b_{i+1}^m}{2}\Delta z_i \tag{42}$$

where the first equation uses the instantaneous value and the second equation uses the trapezoid rule. The master filter can be resampled every time the filter is updated (once for each new frame) which can take longer to compute but is relatively simple to execute. The same filter design described in the uniform-sampling FIR filter can be modified for use with this non-uniform FIR filter scheme.

CONCLUSION

While various inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

Also, various inventive concepts may be embodied as one or more methods, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of" "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The invention claimed is:

1. A spectral imaging system comprising:
a beam splitter to receive an input light beam reflected or scattered from a sample and to split the input light beam into a first portion and a second portion;
a first reflector, in optical communication with the beam splitter, to reflect the first portion of the input light beam;
a second reflector, in optical communication with the beam splitter, to reflect the second portion of the input light beam;
an actuator, operably coupled to the second reflector, to move the second reflector along a propagation direction of the second portion of the input light beam;

a position measurement system, operably coupled to the second reflector, to measure a position of the second reflector;

a detector, disposed at an intersection between the first portion of the input light beam and the second portion of the input light beam, to detect an interference pattern created by the first portion of the input light beam and the second portion of the input light beam; and a processor, operably coupled to the position measurement system and the detector, to generate a spectral image of the sample based at least in part on the position acquired by the position measurement system and the interference pattern acquired by the detector.

2. The spectral imaging system of claim 1, wherein the actuator is configured to place the second reflector at a plurality of non-uniformly spaced positions.

3. The spectral imaging system of claim 1, wherein the actuator is configured to move the second reflector to more than 30 positions per second, and wherein the detector is configured to operate at a frame rate greater than 30 fps.

4. The spectral imaging system of claim 1, wherein the actuator is configured to move the second reflector at a step size substantially equal to or greater than 1 µm.

5. The spectral imaging system of claim 1, wherein the actuator is configured to move the second reflector through a distance of about 0.5 mm to about 3 mm.

6. The spectral imaging system of claim 1, wherein the position measurement system comprises:

a laser, in optical communication with the first mirror and the second mirror via the beam splitter, to transmit a probe laser beam through the beam splitter, the beam splitter directing a first part of the probe laser beam toward the first reflector and a second part of the probe laser beam toward the second reflector; and an array of photodiodes, in optical communication with the first reflector and the second reflector via the beam splitter, to detect a probe interference pattern formed by the first part of the probe laser beam after reflection from the first reflector and the second part of the probe laser beam after reflection from the second reflector.

7. The spectral imaging system of claim 6, wherein the laser source comprises a vertical-cavity surface-emitting laser.

8. The spectral imaging system of claim 6, wherein the probe laser beam has a linewidth of less than 0.1 nm.

9. The spectral imaging system of claim 1, wherein the processor is configured to estimate the spectral image of the sample using at least one of a least squares method, an adaptive sampling method, or an iterative sampling method.

10. The spectral imaging system of claim 1, wherein the actuator is operably coupled to the first reflector to move the first reflector toward a target position.

11. The spectral imaging system of claim 1, wherein the processor is configured to reconstruct a color image from the spectral image by:

passing the spectral image through a set of digital filters, each digital filter including:
  a bandpass filter having a different center wavelength than each other bandpass filter of the set of digital filters; and
  a moving average filter, to generate a set of intermediate images, each intermediate image based on a corresponding black and white image and based on the center wavelength of its corresponding bandpass filter;

generating the color image based on the set of intermediate images.

12. The spectral imaging system of claim 1, wherein the actuator is configured to move the second reflector at a rate greater than 2000 Hz, and wherein the detector is configured to operate at a frame rate greater than 2000 fps.

13. A method of spectral imaging, the method comprising:

splitting an input light beam reflected or scattered from a sample with a beam splitter into a first portion and a second portion;

reflecting the first portion of the input light beam with a first reflector;

reflecting the second portion of the input light beam with a second reflector, the second reflector being at a first position in a plurality of positions along a propagation direction of the second portion of the input light beam;

performing measurement of the first position of the second reflector;

detecting a first interference pattern created by the first portion of the input light beam and the second portion of the input light beam when the second reflector is at the first position;

moving the second reflector to a second position in the plurality of positions along the propagation direction of the second portion of the input light beam performing measurement of the second position of the second reflector;

detecting a second interference pattern created by the first portion of the input light beam and the second portion of the input light beam when the second reflector is at the second position;

generating a spectral image of the sample based at least in part on the measurement of the first position, the measurement of the second position, the first interference pattern, and the second interference pattern.

14. The method of claim 13, wherein the first plurality of positions are non-uniformly spaced along the propagation direction of the second portion of the input light beam.

15. The method of claim 13, wherein moving the second reflector comprises moving the second reflector to more than 30 positions per second, and the method further comprises detecting a plurality of interference patterns at a frame rate greater than 30 fps.

16. The method of claim 13, wherein moving the second reflector comprises moving the second reflector at a step size substantially equal to or greater than 1 µm.

17. The method of claim 13, wherein moving the second reflector comprises moving the second reflector through a distance of about 0.5 mm to about 3 mm.

18. The method of claim 13, wherein performing the measurement of the first position comprises:

directing a first part of a probe laser beam toward the first reflector and directing a second part of the probe laser beam toward the second reflector;

interfering the first part of the probe laser beam after reflection from the first reflector and the second part of the probe laser beam after reflection from the second reflector to form a probe interference pattern;

detecting the probe interference pattern using an array of photodiodes; and estimating the first position of the second reflector based at least in part on the probe interference pattern.

19. The method of claim 18, further comprising:

emitting the probe laser beam from a vertical-cavity surface-emitting laser.

20. The method of claim 18, wherein the probe laser beam has a linewidth less than 0.1 nm.

21. The method of claim 13, wherein generating the spectral image of the sample comprises generating the spectral image using at least one of a least squares method, an adaptive sampling method, or an iterative sampling method.

22. The method of claim 13, further comprising: adjusting at least one of the first reflector or the second reflector toward a target position using a piezoelectric actuator.

23. The method of claim 13, wherein the moving further comprises moving the second reflector at a rate greater than 2000 Hz, and wherein the detecting the first interference pattern and the detecting the second interference pattern is via a detector operating at a frame rate greater than 2000 fps.

24. A spectral imaging system comprising:
   an autocorrelator to create an autocorrelation pattern of an input light beam reflected or scattered from a sample, the autocorrelator comprising:
      a beam splitter to split the input light beam into a first portion and a second portion;
      a first reflector to reflect the first portion of the input light beam;
      a second reflector to reflect the second portion of the input light beam;
      a detector, disposed at an intersection between the first portion of the input light beam and the second portion of the input light beam, to detect an autocorrelation pattern created by the first portion of the input light beam and the second portion of the input light beam;
   a positioning and measurement system operably coupled to the second reflector, the positioning and measurement system comprising:
      an actuator to place the second reflector at a plurality of positions non-uniformly spaced along a propagation direction of the second portion of the input light beam;
      a laser source to emit a probe laser beam toward the beam splitter, the beam splitter directing a first part of the probe laser beam toward the first reflector and directing a second part of the probe laser beam toward the second reflector; and
      an array of photodiodes, in optical communication with the first reflector and the second reflector via the beam splitter, to detect a probe interference pattern formed by the first part of the probe laser beam after reflection from the first reflector and the second part of the probe laser beam after reflection from the second reflector; and
   a processor, operably coupled to the autocorrelator and the positioning and measurement system, to estimate the plurality of positions of the second reflector based at least in part on the probe interference pattern and further to generate a spectral image of the sample based at least in part on the plurality of positions of the second reflector and the autocorrelation pattern of the input light beam.

* * * * *